United States Patent
Shimkets et al.

(10) Patent No.: US 6,610,480 B1
(45) Date of Patent: Aug. 26, 2003

(54) TREATMENT AND DIAGNOSIS OF CARDIAC HYPERTROPHY

(75) Inventors: Richard A. Shimkets, West Haven, CT (US); David G. Lowe, Hillsborough, CA (US)

(73) Assignees: Genentech, Inc., South San Francisco, CA (US); Curagen Corporation, New Haven, CT (US)

( * ) Notice: Subject to any disclaimer, the term of this patent is extended or adjusted under 35 U.S.C. 154(b) by 0 days.

(21) Appl. No.: 09/189,618

(22) Filed: Nov. 9, 1998

Related U.S. Application Data

(60) Provisional application No. 60/065,048, filed on Nov. 10, 1997.

(51) Int. Cl.$^7$ ............................ C12Q 1/68; C07H 21/04
(52) U.S. Cl. ........................ 435/6; 536/23.1; 536/24.31; 536/24.3; 536/25.3
(58) Field of Search ........................ 514/44; 435/320.1, 435/6; 536/23.5, 23.1, 24.31, 24.33, 25.3

(56) References Cited

FOREIGN PATENT DOCUMENTS

WO    WO 97/15690    5/1997

OTHER PUBLICATIONS

Izumo et al., Protooncogene induction and reprogramming of cardiac gene expression produced by pressure overload, 1988, Proc. Natl. Acad. Sci. USA, vol. 85, pp. 339–343.*
He et al., A human brain L–3–hydroxyacyl–coenzyme a dehydrogenase is identical to an amyloid Beta–peptidebinding protein involved in alzheimer'disease, 1998, The Journal of Biological Chemistry, vol. 273, pp. 10741–10746.*
Kennel, Principles and practices of nucleic acid hybridization, 1971, Progr. Nucl. Acid Res. Mol. Biol., vol. 11, pp. 259–301.*
Zink et al., Accession X89234, Dec. 1995.*
Muthukumaran et al., Accession J04694, Oct. 1994.*
Feldman, Can we alter survival in patients with congestive heart failure? *JAMA* 267:1956–1961 (1992).
Konstam, et al., Effects of the angiotension converting enzyme inhibitor enalapril on the long–tem progression of left ventricular dysfunction in patients with heart failure. *Circulation* 86:431–438 (1992).
Shubeita, et al., Endothelelin induction of inositol phospholipid hydrolysis, sacomere assembly and cardiac gene expression in ventricular myocytes. A paracrine mechanism for myocardial cell hypertrophy. *J. Biol. Chem.* 265:20555–20562 (1990).
Chien, et al., Regulation of cardiac gene expression during myocardial growth and hypertrophy: Molecular studies of an adaptive physiologic response. *FASEB J* 5:3037–3046 (1991).
Boheler, et al., Cardiac expression of alpha– and beta–myosin heavy chains and sarcomeric alpha–actins are regulated through transcriptional mechanisms. *J. Biol. Chem.* 267:12979–12985 (1992).

Izumo, et al., Protooncogene induction and reprogramming of cardiac gene expression produced by pressure overload. *Proc. Natl. Acad. Sci. USA* 85:339–343 (1988).
Calderone, et al., Pressure– and volume–induced left ventricular hypertrophies are associated with distinct myocyte phenotypes and differential induction of peptide growth factor mRNAs. *Circulation* 92:2385–2390 (1995).
Boluyt, et al., Alterations in cardiac gene expression during transition from stable hypertrophy to heart failure. Marked upregulation of genes encoding extracellular matrix components. *Circ. Res.* 75:23–32 (1994).
Feldman, et al., Selective changes in cardiac gene expression during compensated hypertrophy and mutation to cardiac decompensation in rats with chronic aortic banding. *Circ. Res.* 73:184–192 (1993).
Buttrick, et al., Alterations in gene expression in the rat heart after pathological and physiological loads. *J. Mol. Cell. Cardiol.* 26:61–67 (1994).
Knowlton, et al., Co–regulation of the atrial natriuretic factor and cardiac myosin light chain–2 genes during alpha–adrenergic stimulation of neonatal rat ventricular cells. *J. Biol. Chem.* 266:7759–7768 (1991).
Pennica, et al., Expression cloning of cardiolipin 1, a cytokine that induces cardiac myocyte hypertrophy. *Proc. Natl. Acad. Sci. USA* 92:1142–1146 (1995).
Mercadier, et al., Myosin isoenzyme changes in several models of rat cardiac hypertrophy. *Circ. Res.* 49:525–532 (1981).
Swynghedauw, Developmental and functional adaptation of contractile proteins in cardiac and skeletal muscle. *Physiol. Rev.* 66:710–749 (1986).
Morgan & Baker, Cardiac hypertrophy. Mechanical, neural, and endocrine dependence. *Circulation* 83:13–25 (1991).
Weber & Brilla, Pathological hypertrophy and cardiac interstitium. Fibrosis and renin–angiotensin–aldosterone system. *Circulation* 83:1849–1865 (1991).
Cooper, IV, Cardiocytes adaptation to chronically altered load. *Ann. Rev. Physiol.* 49:501–518 (1987).

(List continued on next page.)

*Primary Examiner*—Dave T. Nguyen
(74) *Attorney, Agent, or Firm*—Sonnenschein Nath & Rosenthal

(57) ABSTRACT

The present invention is based upon the identification of genes which are differentially expressed in hypertrophic cardiac tissue as compared to normal cardiac tissue. Accordingly, the present invention provides nucleotide sequences of genes selected from the group consisting of CH-1, CH-2, CH-3, CH-4, CH-5, CH-6, CH-7, CH-8, and CH-9, and amino acid sequences of their encoded proteins, as well as derivatives (e.g., fragments) and analogs thereof. The invention also provides therapeutic methods and pharmaceutical compositions which are based on the promotion or inhibition of the function of the differentially expressed genes. The invention further provides methods of diagnosis, prognosis and screening for a disposition for diseases or disorders associated with cardiac hypertrophy. Methods for screening for modulators of the protein products of the differentially expressed genes in cardiac hypertrophy tissue are additionally provided.

28 Claims, 10 Drawing Sheets

OTHER PUBLICATIONS

Murakami, et al., Cloning of antienzyme inhibitor, a highly homologous protein to ornithine decarboxylase. *J. Biol. Chem. 271(7)*:3340–3342 (1996).

Wegrowski, et al, The murine biglycan: Complete cDNA cloning, genomic organization, promoter function, and expression. *Genomic 30(1)*:8–17 (1995).

Dreher, et al., Vascular smooth muscle biglycan represents a highly conserved proteoglycan with the arterial wall. *Eur. J. Cell Biol. 53(2)*:296–304 (1990).

Walchli, et al., Tissue–specific expression of the fibril–associated collagens XII and XIV. *J. Cell Sci. 107(Pt 2)*:669–681 (1994).

Tamura, et al., Cyclin G: A new mammalian cyclin with homology to fission yeast Cig1. *Oncogene. 8(8)*:2113–2118 (1993).

Lockard and Bloom, Trans–cellular desmin–lamin B intermediate filament network in cardiac myocytes. *J. Mol. Cell Cardiol. 25*:303–309 (1993).

van Groningne, et al., Rat desmin gene structure and expression. *Biochim. Biophys. Acta 1217*:107–109 (1994).

Watson, et al., Desmin gene expression in cardiac myocytes is responsive to contractile activity and stretch. *Am. J. Physiol. 270(4 Pt1)*:C1228–1235 (1996).

Maeda, et al., Analysis of an expression profile of genes in human adipose tissue. *Gene 190(2)*:227–235 (1997).

Englemann, et al., Immediate postnatal rat heart development modified by abdominal aortic banding: Analysis of gene expression. *Mol. Cell Biochem. 163–164*:47–56 (1996).

Bhalerao, et al., Molecular cloning, characterization, and genetic mapping of the cDNA coding for a novel secratory protein of mouse. *J. Biol. Chem. 270(27)*:16385–16394 (1995).

Legon, et al., The structure and function of the proenkephalin gene, *Nucleic Acids Res. 10*:7905–7918 (1982).

Konig, et al., Pain responses, anxiety and aggression in mice deficient in pre–proenkephalin. 0*Nature 383*:535–538 (1996).

Johnson, et al, The role of transglutaminase in the rat subtotal nephrectomy model of renal fibrosis. *J. Clin. Invest. 99(12)*:2950–2960 (1997).

Nurminskaya & Linsenmayer, Identification and characterization of up–regulated genes during chondrocyte hypertrophy. *Dev. Dyn 206(3)*:260–271 (1996).

Reinhard, et al., VASP interaction with vinculin: A recurring theme of interactions with proline–rich motifs. *FEBS Lett. 399(1–2)*:103–107 (1996).

Macalma, et al., Molecular characterization of human zyxin. *J. Biol. Chem. 271(49)*:31470–31478 (1996).

Goldspiel et al., Human Gene Therapy. *Clinical Pharmacy 12*:488–505 (1993).

Mulligan, The basic science of gene therapy. *Science 260*:926–932 (1993).

Simpson, et al., Transcription of early developmental isogenes in cardiac myocytes hypertrophy. *J. Mol. Cell. Cardiol. 21(Suppl. 5)*:79–89 (1989).

Chien, et al., Regulation of cardiac gene expression during myocardial growth and hypertrophy: Molecular studies of an adaptive physiological response. *FASEB J. 5*:3037–3046 (1991).

Schneider & Parker, Modulation of cardiac genes by mechanical stress: The oncogene signaling hypothesis. *Mol. Biol. Med. 8*:167–183 (1991).

Iwaki, et al., Multiple mRNAs from rat brain alpha–crystalline B chain result from alternative transcriptional initiation. *J. Biol. Chem. 265*:13809–13817 (1990).

Lee, et al., Alpha 1–adrenergic stimulation of cardiac gene transcrption in neonatal rat myocardial cells. Effects on myosin light chain–2 gene expression. *J. Biol. Chem. 263*::7352–7358 (1988).

Lai, et al., Prostaglandin F2 induces cardiac myocyte hypertrophy in vitro and cardiac growth in vivo. *Am. J. Physiol. 271*:H2197–H2208 (1996).

Lompré, et al., Changes in gene expression during cardiac growth. *Int. Rev. Cytol. 124*:137–186 (1991).

Izumo, et al., Protooncogene induction and reprogramming of cardiac gene expression produced by pressure overload. *Proc. Natl. Acad. Sci. USA 85*:339–343 (1988).

Cummins, Transitions in human atrial and ventricular myosin light–chain isoenzyme in response to cardiac–pressure–overload—induced hypertrophy. *Biochem J. 205*:195–204 (1982).

Ingwall, et al., The creatine kinase system in normal and diseased human myocardium. *N. Engl. J. Med. 313*:1050–1054 (1985).

Samuel, et al., Accumulation of fetal fibronectin mRNAs during the development of rat cardiac hypertrophy induced by pressure overload. *J. Clin. Invest. 88*:1737–1746 (1991).

Komuro, et al., Expression of cellular oncogenes in the myocardium during the developmental stage and pressure–overloaded hypertrophy of the rat heart. *Circ. Res. 62*:1075–1079 (1988).

Mercadier, et al., Altered sarcoplasmic reticulum Ca(2+)–ATPase gene expression in the human ventricle during end–stage heart failure. *J. Clin. Invest. 85*:305–309 (1990).

Rockman, et al., Segregation of atrial–specific and inducible expression of an atrial natriuretic factor transgene in an in vivo murine model of cardiac hypertrophy. *Proc. Nat. Acad. Sci. USA 88*:8277–8281 (1991).

Kimura, et al., Sarcoplasmic reticulum function in skinned fibers of hypertrophied rat ventricle. *Heart Circ. Physiol. 25*:H1006–H1011 (1989).

Batra & Rakusan, Capillarization of the hypertrophic heart: Discrepancy of the results obtained by the triangulation and domain methods. *J. Cardiovasc. Pharmacol. 17(Suppl 2)*:S151–S153 (1991).

Chapman, et al., Regulation of fibrillar collagen types I and III and basement membrane type IV collagen gene expression in pressure overloaded rat myocardium. *Circ. Res. 67*:787–794 (1990).

Schonherr, et al., Induction of biglycan with type I collagen. *J. Biol. Chem. 270*:2776–2783 (1995).

Heimer, et al., TGF–beta modulates the synthesis of proteoglycans by myocardial fibroblasts in culture. *J. Mol. Cell. Cardiol. 27*:2191–2198 (1995).

Delcayre, et al., Synthesis of stress proteins in rat myocytes 2–4 days after imposition of hemodynamic overload. *J. Clin. Invest. 82*:460–468 (1988).

Komuro, et al., Molecular cloning and characterization of a Ca2++Mg2+–dependent adenosine triphosphate from rat cardiac sarcoplasmic reticulum. Regulation of its expression by pressure overload and developmental stage. *J. Clin. Invest. 83*:1102–1108 (1989).

Nagai, et al., Regulation of myocardial Ca2+–ATPase and phospholamban mRNA expression in response to pressure overload and thyroid hormone. *Proc. Natl. Acad. Sci. USA 86*:2966–2970 (1989).

De la Bastie, et al., Function of the sarcoplasmic reticulum and expression of its Ca2+–ATPase gene in pressure over–load–induced cardiac hypertrophy in the rat. *Circ. Res. 66*:554–564 (1990).

* cited by examiner

PANEL A 1 ggtacctgmn tggccaagaa gttgcgmant ttgtntggna gagtggtaag cagtggggtg
61 gcaaacagac ctggagcaat tgttaccaca cggatgccta taggagcnag atct

PANEL B

QUERY: 114 AGATCTNGCTCCTATAGGCATCCGTGTGGTAACAATTGCTCCAGGTCTGTTTGCCACCCC 55
            |||||| ||||||||||||||||||||||||||||||| ||||||||||||||||||||||
SBJCT: 665 AGATCTGGCTCCTACAGGCATCCGTGTGGTAACAATTGCGCCAGGTTTGTTTGCCACCCC 724

QUERY: 54 ACTGCTTACCACTCTNCCANACAAANTNCGCAACTTCTTGGCCANCCAGGTACC 1
           ||||||||||||||| ||| ||||| ||||||||||||||| |||||||||||
SBJCT: 725 ACTGCTTACCACCCTTCCAGAGAAAGTGCGAAACTTCTTGGCCAGCCAGGTACC 778

PANEL C

QUERY: 113 GATCTNGCTCCTATAGGCATCCGTGTGGTAACAATTGCTCCAGGTCTGTTTGCCACCCCA 54
            ||||| ||||||| ||||||||||||||||||||| |||| ||||||||||||||||||
SBJCT: 568 GATCTGGCTCCCCATAGGTATCCGGGTGATGACCATTGCCCCAGGTCTGTTTGGCACCCCA 627

QUERY: 53 CTGCTTACCACTCTNCCANACAAANTNCGCAACTTCTTGGCCANCCAGGTACC 1
           ||||||||||||| || ||| ||| ||||||||||||||| |||| ||||
SBJCT: 628 CTGCTGACCAGCCTCCCAGAGAAAGTGCAACTTCTTGGCCAGCCAAGTGCC 680

Fig. 2

PANEL A

```
  1 rgatccaggg aatcctgcag ttccaggagg accaggggga cctggttgcc cgtcactgcc
 61 ccgagcacca tcattgcctc gagcacctgc ggctccagga agacctggtc gtcctcgctc
121 accaggagcc cctctgggac ccatgggggcc aggagctccg ttgtctcccg gaagaccgtt
181 ttcacccttc aatccagg
```

PANEL B

```
QUERY:  197 CCTGGGATTGAAGGGGTGAAAAACGGTCTTCCGGGAGACAACGGAGCTCCTGGCCCCATGGGT 138
            |||||||||||||||||||| |||||| ||||||||||||||||||||||||||||||||||
SBJCT:  857 CCTGGACTGAAGGGGTGAAAATGTTCTTCCAGGAGACAACGGAGCTCCTGGCCCCATGGGT 916

QUERY:  137 CCCAGAGGGGCTCCTGGTGAGCGAGGACGACCAGGTGTCTTCCTGGAGCCGACCAGGTGCTCGA 78
            |||||||||||||||||||||||||||||||||||| ||||||||||||||||||||||||
SBJCT:  917 CCTAGAGGGGCTCCTGGTGAGCGAGGACGACCAGGCCTTCCTGGAGCTGCAGGTGCTCGA 976

QUERY:   77 GGCAATGATGGTGCTCGGGGCAGTGACGGGGCAACCAGGTCCCCCTGGTCCTCCTGGAACT 18
            ||||||||||||||||||||||||||||||||| |||||||||||||||||||||||||
SBJCT:  977 GGCAATGATGGTGCTCGGGGCAGTGATGGGCAACCTGTTCCCCCTGGCCCTCCTGGAACT 1036

QUERY:   17 GCAGGATTCCCCTGGATC 1
            ||||||||||||||||||
SBJCT: 1037 GCAGGATTCCCCTGGATC 1053
```

Fig. 3

PANEL A

```
  1  tccggagtgg acagccagta ggagtagtcg ttcctggagg cgaagttgca gacgttgttg
 61  atgttgcaga agaggaaggg catggtgctg aacttgcgca gacagctgcc agccgtaccc
121  aagtcctgac catggcccg ctcgtttcct tggacataga gcagagagta cccatggtaa
181  agaattttgg tccctgggg acacagcggg tcatctcacn gtctgactat gcctggtcac
241  aaggaagcca tgtccacag atggggtacc
```

PANEL B

```
QUERY:  270  GGTACCCCATCTGTGACCACCATGGCTTCCTTGTGACCAGGCATAGTCAGACNGTGAGATGA  211
SBJCT: 4443  GGTACCCCATCTGTGACCACCATGGCTTCCTTGTGACCAGGCATAGTCAGAC  AGATGA  4501
             GGTACCCCATCTGTGACCACCATGGCTTCCTTGTGACCAGGCATAGTCAGACAAC-AGATGA

QUERY:  210  CCCGCTGTGTCCCCCCAGGGACCAAAAATTCTTTACCATGGTACTCTCTGCTCTATGTCCA   151
SBJCT: 4502  CCC CTGTGTCCCCCAGGGACCAAAAATTCTTTACCATGG TACTCTCTGCTCTATGTCCA
             CCCACTGTGTCCCCCAGGGACCAAAAATTCTTTACCATGGATACTCTCTGCTCTATGTCCA   4561

QUERY:  150  AGGAAACGAGCGGGCCCATGGTCAGGACTTGGGTACGGCTGGCAGCTGTCTGCGCAAGTT    91
SBJCT: 4562  AGG AACGAGCG GCCCA GG CAGGACTTGGGTACGGCTGGCAGCTG CTGCG AAGTT
             AGGCAACGAGCGTGCCCACGCGGTGCCCACGGGGCAGGACTTGGGTACGGCTGGCAGCTGGCCTGCTGCGTAAGTT  4621

QUERY:   90  CAGCACCACCATGCCCTTCCTCTCTGCAACATCAACAACGTCTGCAACTTCGCCTCCAGGAA  31
SBJCT: 4622  CAGCACCACCATGCCCCTT CTCTTCTGCAACATCAACATCAACAACGTCTGCAACTTCGCCTCCAGGAA
             CAGCACCACCATGCCCTTCTCTTCTGCAACATCAACATCAACAACGTCTGCAACTTCGCCTCCAGGAA  4681

QUERY:   30  CGACTACTCCTACTGGCTGTCCACTCCGGA    1
SBJCT: 4682  CGACTACTC TACTGGCTGTCCAC CC GA
             CGACTACTCTTACTGGCTGTCCACGCCCAGA  4711
```

Fig. 4

PANEL A

```
  1 ggtaccttcn atttgttccc atgctatcnn atccntaagg atgccctggt ttcccagcca
 61 ncnnagtgtc tgcacccngn aggattgcct gctgnctntn cnntgactttt tctgttccgg
121 a
```

PANEL B

```
QUERY:    1 GGTACCTTCNATTTGTTCCCATGCTATCNNATCCNTAAGGATGCCCTGGTTTCCCAGCCA  60
            |||||||||| |||||||||||||||||  ||| |||||||||||||||||||||||||
SBJCT:  687 GGTACCTTCAATGTGTTCCATGTTACCAACTCCATAAAGATGCCCTGGTTTCCCAGCCA  746

QUERY:   61 NCNNAGTGTCTGCACCCNGNAGGATTGCCTGCTGNCTNTNCNNTGACTTTTCTGTTCCGG 120
            |  ||||||||||||| | |||| |||||||| |||  |||| ||||||||  |||||
SBJCT:  747 ACCAGGTACTTGCACCCAGAAGGATTGCCCTCCGACTACACAATCAGTTTTCTATTCCGG 806

QUERY:  121 A 121
            |
SBJCT:  807 A 807
```

Fig. 5

PANEL A

```
  1  yggccacggc ggcctgcggg gcntnancgg gtttcctca gggcaaatga tataaggctc
 61  ggtacc
```

PANEL B

```
QUERY:   1  GGCCACGGGGGGCCTGCGGGCN-TNANCGGGTTTTCCTCAGGGCAAATGATAT-AAGGCT   58
SBJCT: 186  GGCCACGGCGG CT CG GGC T  CGGGTTTT TCAGG CAAATGAT   AAGG  T
            GGCCACGGGCGGTCTCCGAGGCTATCTACGGGTTTTTTTCAGGACAAATGATGCGAAGGT  245

QUERY:  59  CGGTAC  64
            GGTAC
SBJCT: 246  -GGTAC  250
```

Fig. 6

PANEL A

```
  1  gtgcacacac actatagttt tcctgcttgt ccttnngttc tctctgggag atggacaacc
 61  ctcaaaggca ctgattgntg acattnntag ctctgntcct tactcaggca gccagctcag
121  ccaaggcccg gtccaaggga tcc
```

PANEL B

```
QUERY:  143  GGATCCCTTGGACCGGGCCCTTGGCTGAGCTGGCCTGCCTGAGTAAGGANCAGAGCTANNAA   84
SBJCT: 2175  GGATCC TTGGACCGGGCCCTTGGCTGAGCTGAGCTGGCCTGCCTGAGTAAGGA CA AGC A  AA

QUERY:   83  GGATCCTTTGGACCGGGCCCTTGGCTGAGCTGGCCTGCCTGAGTAAGGACCA-AGCCATCAA 2233
SBJCT: 2234  TGTCANCAATCAGTGCCTTTGAGGGTTGTCCATCTCCCAGAGAACNNAAGGACAAGCA       24
             TGTCA CAATCAGTGCCTTTGAGGGTTGTCCATCTCCCA AGA A C  A GG CAAGCA
             TGTCACCAATCAGTGCCTTTGAGGGTTGTCCATCTCCCAAAGACATCATATGG-CAAGCA 2292

QUERY:   23  GGAAAACTATAGTGTGTGTGCAC    1
SBJCT: 2293  GGAAAACTAT  TGTGTG GC C
             GGAAAACTATGATGTGTGCGCGC 2315
```

Fig. 7

PANEL A

```
  1  rgatcccaag tcacagcatt ttcccacgta actcgactct gaggccatag cctatccaca
 61  gcctcctcgt ccccctgcacc gcccagtgtc tcactggctg tgttggagac gggaattgca
121  taagctt
```

PANEL B

```
QUERY:    1  RGATCCCAAGTCACAGCATTTTCCCACGTAACTCGACTCTGAGGCCATAGCCTATCCACA    60
             +|||||||||||||||||||||||||||||||||||||||||||||||||||||||||||
SBJCT: 1149  AGATCCCAAGTCACAGCATTTTCCCACGTTACTCGACTCTGAGGCCATAGCCTATCCACA  1208

QUERY:   61  GCCTCCTCGTCCCCTGCACCGCCCAGTGTCTCACTGGCTGTGTTGGAGACGGGAATTGCA   120
             ||||||||||||||||||||||||||||||||||||||||||||||||||||||||||||
SBJCT: 1209  GCCTCCTCGTCCCCTGCACCGCCCAGTGTCTCACTGGCTGTGTGTTGGAAACGGGAATTGCA  1268

QUERY:  121  TAAGCTT   127
             |||||||
SBJCT: 1269  TAAGCTT  1275
```

Fig. 8

PANEL A

```
  1 aagcttgcac agatcaaaag aaatgtgaacc gtgtggggac aaggcaaata aaaaaactca
 61 cggtgcnatt ctcnncataa agcgaaacgg tttaaatgca gcagtgtgan ttcttcccan
121 ttccttctct gggatttcag gggatcc
```

PANEL B

```
QUERY:  147 GGATCCCCTGAAATCCCAGAGAAGGAAGAANTCACACTGCTGCATTTAAACCG   88
            GGATCCCCTGAAATCCCC GAGAAG      TGGGAAGAA TCA ACTG TGCATTTAA  CG
SBJCT: 3254 GGATCCCCTGAAATCCCGGAGAAGAGCCTGGAAGAA-TCAAACTGATGCATTTAACGCG 3312

QUERY:   87 TTTCGCTTTATGNNGAGAATNGCACCGTGAGTTTTTTTATTTGCCTTGTCCCCACACGGT  28
            TT GCTTTA     GAG AT GCACCGTGAG      T  TAT TG C TGTCCCACACGGT
SBJCT: 3313 TTTCGCTTTACACAGAGGATCGCACCGTGAGCCGTGCTATCTGTCCCCACACGGT 3372

QUERY:   27 TCCATTTCTTTTGATCTGTGCAAGCTT    1
            TC  TTTCTTTG  TCTGTGCAAGCTT
SBJCT: 3373 TCTGTTTCTTTTGGTCTGTGTGCAAGCTT 3399
```

Fig. 9

PANEL A

```
  1  gtgcacggac tgmaggctgt gctcgggcca gtggtgactg catttgccac aggactcatt
 61  tactgccacg ctctgcctct gangtnntc cangtncnnn annanntnan nggtnanntn
121  ntncaaatnt tncaactncn tnaaggtnaa ngggnctggg ctncaagaga acgtanctgg
181  tttggtttt gagatggtgg aggcagtggg tgctgcttct cttgaactag gggcttctcc
241  ttctgctgag cataggtgaa gctagc
```

PANEL B

```
QUERY:  265  CTAGCTTCACCTATGCTCAGCAGAAGGAGAAGCCCCTAGTTCAAGAGAAGCAGCACCCAC   206
             CTAGCTTCACCTATGCTCAGCAGAAGAGAAGAAGCCCCTAGTTCAAGAGAAGCAGCACCCAC
SBJCT: 1173  CTAGCTTCACCTATGCTCAGCAGAAGAGAAGAAGCCCCTAGTTCAAGAGAAGCAGCACCCAC  1232

QUERY:  205  TGCCTCCACCATCTCAAAACCAAAAACCAGNTACGTTCTCTTGNAG--CCCAGNCCCNTTNA   147
             GCCTCCACCA CTCAAAACCAAAACCAG TACG TCTC TG AG CCCAG CCC TT A
SBJCT: 1233  AGCCTCCACCAGCTCAAAACCAAAAACCAGTACGCTCTCCTGGAGGCCCAGCCCCCTTGA   1292

QUERY:  146  CCTTNANGNAGTGNAAANATTTGNANNANNTNACCNNTNANNTNNTNNNGNACNTGGANN   87
             CC T A G AG T  A  A TTG A  A  T ACC     A T T  G AC TGGA
SBJCT: 1293  CCCTGAAGGAGTAGAGGAGTTGGAGCAGCTGACCCAGCTGATGCAGGACATGGAAC      1352

QUERY:   86  ACCNTCAGAGGCAGAGCGTGGCAGTAAATGAGTCCTGTGGCAAATGCAGTCA-CCACTGG   28
             ACC TCAGAGGCAGAGCGTGGCAGT AATGAGTCCTGTGGCAAATGCA TCA CCACTGG
SBJCT: 1353  ACCCTCAGAGGCAGAGCGTGGCAGTGAATGAGTCCTGTGGCAAATGCAATGCAGCCACTGG  1412

QUERY:   27  CCCGAGCACAGCCTNCAGTCCGTGCAC   1
             CCCG GCACAGCCT C GT CGTGCAC
SBJCT: 1413  CCCGTGCACAGCCTGCGGTTCGTGCAC  1439
```

TREATMENT AND DIAGNOSIS OF CARDIAC HYPERTROPHY

CROSS-REFERENCE TO RELATED APPLICATION

This application claims the benefit of U.S. Provisional Application No. 60/065,048, filed Nov. 10, 1997.

FIELD OF THE INVENTION

The present invention relates to genes which are differentially expressed in hypertrophic cardiac tissue as compared to normal cardiac tissues. The present invention further relates to the CH-1, CH-2, CH-3, CH-4, CH-5, CH-6, CH-7, CH-8 and CH-9 genes, which genes have nucleotide homology to, but are not identical to human short-chain alcohol dehydrogenase, mouse amyloid β-peptide binding protein, mouse α-1 Collagen Type III, mouse α-1 Collagen Type IV, chicken Collagen Type XIV, human 13kD DAP, mouse and human Gelsolin, mouse Osteonectin, mouse Transglutaminase, and mouse and human Zyxin, the proteins encoded by these genes, and derivatives and analogs thereof. This invention further provides methods of treating or preventing cardiac hypertrophy based on use of genes and the products of genes differentially expressed in hypertrophic cardiac tissue as compared to normal cardiac tissue. Additionally, the invention relates to methods of diagnosis, prognosis as well as methods of screening for modulators of the above listed proteins that are protective for cardiac hypertrophy.

BACKGROUND OF THE INVENTION

Heart failure is often defined as the inability of the heart to deliver a supply of oxygenated blood sufficient to meet the metabolic needs of peripheral tissues, both at rest and during exercise. See generally, Hutter, Jr., "Congestive Heart Failure", in Scientific American: Medicine, Volume 1 (1:II), eds. Dale and Federman (Scientific American, Inc. 1994). Heart failure is a common outcome of hypertension or post-myocardial infarction and is a major contributor to cardiovascular morbidity and mortality. The clinical presentation of heart failure is an energy deprived heart, with altered calcium ion homeostasis, energy metabolism, and decreased contractile reserve (see e.g, Ingwall, *Circulation* 87 (Suppl VII):58–62 (1993)).

Hypertrophy develops in response to chronic overloading of the heart, such as occurs in systematic hypertension or aortic stenosis. Hypertrophy entails an increase both in size of the individual muscle cells and in the overall muscle mass. While cardiac hypertrophy is thought to be an initial compensatory response to increased hemodynamic load, restoring lost function and normalizing wall stress, hypertrophy is also an independent risk factor for progression to decompensated heart failure (Kannel, in *Congestive Heart Failure* W. KT, Ed. (WB Saunders Co, 1989) pp. 1–9; A. M. Feldman, *JAMA* 267:1956–61 (1992); Katz, *TCM* 5:37–44 (1995); Konstam, et al., *Circulation* 86:431–438 (1992); Shubeita, et al., *J. Biol. Chem.* 265:2055–20562 (1 990)). Clinical trials in heart failure with angiotensin converting enzyme inhibitors suggest that part of the benefit of these inhibitors derives from attenuation of cardiac hypertrophy, structural remodeling and fibrosis (Chien et al., *FASEB J.* 5:3037–3046 (1991); Boheler et al., TCM2:176–182 (1992)).

Experiments in animal model systems and cell culture have demonstrated that cardiac hypertrophy is associated with changes in gene expression (Izumo et al., *Proc. Natl. Acad. Sci. USA* 85:339–343 (1988); Calderone et al., *Circulation* 92: 2385–2390 (1995); Boluyt, et al., *Circ. Res.* 75:23–32 (1994); Feldman et al., *Circ. Res.* 73:184–192 (1993); Buttrick et al., *J. Mol. Cell. Cardiol.* 26:61–67 (1994)). The specific pattern of expression differences in vivo, referred to as the molecular phenotype, is dependent on the nature of the hypertrophic stimulus, as well as the stage of compensatory hypertrophy or decompensated failure (Knowlton, et al.,*J. Biol. Chem.* 266:7759–7768 (1991); Shubeita, et al., *J. Biol. Chem.* 265:20555–20562 (1990); Pennica, et al., *Proc. Natl. Acad. Sci. USA* 92:1142–1146 (1995); Lai, et al., *Am. J. Physiol.* 271:H2197–H2208 (1996); Eppenberger et al., *TCM* 4:187–193 (1994); Ito et al., *J. Clin. Invest.* 92:398–403 (1993)). Studies with cultured cardiomyocytes and non-myocytes have also suggested a role for specific mediators in the response to increased hemodynamic load including adrenergic stimulation, gp130 signaling, endothelin-1, angiotensin II, and prostaglandin F2α, each with a distinct expressional and phenotypic response (Anversa et al., *J. Mol. Cell. Cardiol.* 12:781–795 (1980)).

Pressure overload leads to myocardial hypertrophy and the remodeling of muscular and collagenous compartments of the myocardium where the accumulation of fibrillar collagen is known to impair myocardial stiffness. Pressure overload can be achieved via surgical constriction of the aorta, aortic incompetence and aortocaval fistula (Mercadier et al., *Circ. Res.* 49:525–532 1981)). After abdominal aortic banding, left ventricular weight rises early and reaches a plateau by day 3 (Lindy et al., *Circ. Res.* 20:205–209 (1972); Turto, *Cardiovasc. Res.* 11:358–366 (1977)). Fibroblast proliferation also occurs with pressure overload, starting at day 2 and declining at day 7 after abdominal aortic banding (Morkin et al., *Am. J. Physiol.* 215:1409–1413 (1968)). Pressure overload caused cardiac hypertrophy is also associated with changes in gene expression (Lompre et al., *Int. Cell Rev.* 124:137–186 (1990); Schwartz et al., *Heart Failure* 4:154–163 (1988)). For instance, cardiac hypertrophy secondary to pressure overload is accompanied by induction of two contractile protein isogenes, B-myosin heavy chain and skeletal actin (Swynghedauw,*Phydiol. Rev.* 66:710–749 (1986)).

Current clinical and preclinical work suggests that cardiac hypertrophy and heart failure are problems of cardiac growth and morphogenesis. A comprehensive understanding of the molecular phenotype in compensatory and pathological hypertrophy may thus be important to developing novel therapeutic strategies as well as understanding current treatments. However, the technical limitations of the candidate gene paradigm, in which specific genes of interest have been tested one or several at a time for their association with heart disease, mean that relatively little information is available compared to the entire complement of genes expressed in the myocardium.

To obtain a more detailed understanding of the changes in gene expression occurring during pressure overload hypertrophy, the present inventors have used quantitative expression analysis (QEA) to identify expression differences in a rat surgical model of pressure overload (POL) induced cardiac hypertrophy. Abdominal aortic constriction leads to moderate hemodynamic overload (Boheler and Schwartz, TCM2:176–182 (1992); Grossman et al., *J. Clin. Invest.* 56:56–64 (1975)), with the heart responding by concentric hypertrophy of the left. ventricle, a process that leads to normalization of systolic wall stress (Morgan and Baker, Circulation 83:13–25 (1991)). Although increased load is thought to be the primary stimulus for this response, focal necrosis in the myocardium may also contribute to increased wall stress in this model.

This in vivo model is attractive for expression analysis as there are limited changes in tissue cellularity by infiltration of non-resident cells. The tissue reaction to acute POL is primarily due to an intrinsic response of the myocardium including hypertrophy of the cardiomyocytes, in addition to hyperplasia of endothelial, smooth muscle, and mesenchymal cells (Weber and Brilla, Circulation 83:1849–1865 (1991); Cooper, IV, Ann. Rev. Physiol. 49:501–518 (1987)). While this process is initially adaptive, there is ultimately a deterioration of contractile function accompanied by interstitial and perivascular fibrosis and increased wall stiffness (Kimura et al., Heart Circ. Physiol. 25:H1006–H1011 (1989); Batra and Rakusan, J. Cardiovasc. Pharmacol. 17 (Suppl 2):S151–S153 (1991)).

(1) Proteins Differentially Expressed in Hypertrophic Cardiac Tissue

The present inventors identified the following genes that are differentially expressed in cardiac hypertrophic tissue as compared to normal cardiac tissue: genes similar to the genes encoding human short-chain alcohol dehydrogenase, mouse amyloid beta-peptide binding protein, mouse α-1 Collagen Type III, mouse α-1 Collagen Type IV, chicken Collagen Type XIV, human 13kD DAP, mouse and human Gelsolin, Osteonectin, mouse Transglutaminase, and mouse and human Zyxin. The present inventors also discovered that the following genes were differentially regulated in the hypertrophic tissue: α-Enolase, Antizyme Inhibitor, Biglycan, Cytochrome Oxidase I, Cytochrome Oxidase II, Cyclin G, D-binding protein, Desmin, Fibrillin, Laminin, Protein kinase C-binding protein β15, p85, 28S rRNA gene, genes for 5.8S, 18S, and 28S RRNAS, and Preproenkephalin. The present inventors also identified the following genes which previously have been shown to be differentially expressed in hypertrophic cardiac tissue: α Skeletal Actin, ANF, ANF precursor, Atrial Natriuretic Peptide (ANP), MLC2, α Cardiac to MHC, β Cardiac MHC, and Fibronectin.

Antizyme inhibitor is a regulator of antizyme, an enzyme that accelerates the degradation of ornithine decarboxylase (ODC) by the 26 S proteasome. Antizyme inhibitor binds to the antizyme with a higher affinity than does ODC, effecting ODC release from an ODC-antizyme complex. Antizyme inhibitor contains amino acid residues required for formation of active sites of ODC, but it completely lacks ODC activity (Murakami et al., J. Biol. Chem. 271(7):3340–3342 (1996)).

Biglycan is a proteoglycan containing one or more glycosaminoglycans moieties (GAG) which are predominantly associated with the extracellular matrix (ECM). In one study, the lowest biglycan mRNA expression in mice was located within the heart, skin and kidney, while the highest was in the lungs, liver and spleen (Wegrowski et al, Genomic 30(1):8–17 (1995)). The extracellular matrix proteins collagen, fibronectin, and laminin influence biglycan mRNA expression (Dreher et al., Eur. J. Cell Biol. 53(2):296–304 (1990)).

Collagen III is distributed in skin, blood vessels, and internal organs. Chronic hypertension is known to affect collagen levels (Burgess et al., Am. J. Physiol. 270(1 Pt 2):H151–159 (1996)). Collagen III is also necessary for Collagen I fibrillogenesis in the cardiovascular region (Lui et al., Proc. Natl. Acad. Sci. USA 94(5):1852–1856 (1997)). The ratio between collagen III/I mRNA is a marker for changes in the extracellular matrix associated with hypertrophy (MRNA levels used as indicators).

Collagen XIV localizes near the surface of collagen fibrils and may be involved in epithelial-mesenchymal interactions as well as in the modulation of tissue biomechanical properties (Berthod et al., J. Invest. Dermatol. 108(5):737–742 (1997)). Collagen XIV is expressed at very few sites in the 6-day-old embryo, but occurs in virtually every collagen I-containing tissue (skeletal muscle, cardiac muscle, gizzard, tendon, periosteum, nerve) by the end of embryonic development (Walchli et al., J. Cell Sci. 107(Pt 2):669–681 (1994)).

Cyclin G contains a typical cyclin box at the N-terminus but no apparent "destruction box" or "PEST" sequence. Interestingly, in its C-terminus region, Cyclin G has a sequence homologous with a tyrosine phosphorylation site of the epidermal growth factor receptor. Although this cyclin is phylogenetically related to HCS26 of Saccharomyces cerevisiae, it most resembles Cig1, a B-type cyclin, of Schizosaccharomyces pombe, which has been suggested to act at the G1/S phase of the cell cycle. Cyclin G mRNA is induced within 3 hours of growth stimulation and remains elevated with no apparent cell cycle dependency (Tamura et al., Oncogene. 8(8):2113–8, (1993)).

Cytochrome C oxidase subunits I and II are two of three mitochondrial DNA encoded subunits of respiratory Complex IV (Kadenbach et al., 1983, Schoffner et al., 1995). Complex IV is located within the mitochondrial inner membrane and is the third and final enzyme of the electron transport chain of mitochondrial oxidative phosphorylation (Id.)

Desmin, an intermediate filament protein, is considered a differentiation marker for all muscle types (van Groningen et al., Biochi. Biophy. Acta 1217(1):107–109 (1994)). It is distributed throughout the cytoplasm of smooth muscle cells—linking together adjacent myofibrils in heart and skeletal muscle cells. Because desmin is an intermediate filament, it can withstand larger stretching forces than actin or microtubules—thereby providing tensile strength and support for the rest of the muscular system. It has been shown that contractile activity and load due to passive stretch increase desmin content in neonatal rat cardiac myocytes through increased desmin gene transcription (Watson et al., Am. J. Physiol. 270(4 Pt1):C1228–1235 ((1996)).

Fibrillin fibers are large glycoproteins that are incorporated in the outer casing of elastic fibers found within most connective tissues. Fibrillin proteins are essential for the integrity of the elastic fibers; and a mutation in the gene results in Marfan's Syndrome (Watkins et al., Circ. Res. 60:327–336 (1987); Lockard and Bloom, J. Mol. Cell Cardiol. 25:303–309 (1993)).

Gelsolin is a calcium- and phospholipid-dependent modulator of actin. Gelsolin is also considered a marker for oligodendrocytes (Tanaka et al., Glia 19(4):286–297 (1997)), and has been shown to be active in adipose tissue (Maeda et al., Gene 190(2):227–235 (1997)).

Laminin protein is a part of the extracellular matrix, specifically an integral part of the basal lamina which endothelial cells themselves secrete (Eghbali, et al., J. Mol. Cell. Cardiol. 21:103–113 (1989)). Associated with angiogenesis, it is a fibrous protein similar to fibronectin. Laminin is related to other structural proteins—collagen III (blood vessel tissue), collagen IV (basal lamina "basement" membrane), and fibronectin (Engelmann et al., Mol. Cell Biochem. 163–164:47–56 (1996); Sage, *Nature Med.* 3:144–146 (1997)).

Secreted Protein Acidic and Rich in Cysteine (SPARC)/Osteonectin is a $Ca^{+2}$ binding glycoprotein which binds to collagen. When SPARC is added to synovial fibroblasts, 3 metalloproteinase mRNAs, including collagenase, stromelysin, and gelatinase were upregulated, all of which degrade the ECM and basal laminae (Tremble et al *J. Cell Biol.* 121(6):1433–1444 (1993)).

The p85/ECM1 sequence has not been reported, but it has been reported to have a structural similarity to serum albumin family proteins and to Endo16 (a calcium-binding protein of sea urchin) particularly because of typical cysteine doublets (Bhalerao et al., *J. Biol. Chem.* 270(27):16385–94, (1995)).

Met-enkephalin and leu-enkephalin are pentapeptides which compete for and mimic the effect of opiate drugs (Legon et al., *Nucleic Acids Res.* 10:7905–7918 (1982)). Preproenkephalin mRNA encodes 4 copies of Met-enkephalin, 2 copies of Met-enkephalin extended sequences, and 1 copy of leu-enkephalin (Comb et al., *Nature* 296:663–666 (1982)). Enkephalin-deficient mice were healthy, fertile, and cared for their offsprings but displayed significant behavior abnormalities (Konig et al, *Nature* 383:535–538 (1996)).

Transglutaminase (TGase) is a calcium-dependent enzyme which is expressed in a variety of cells and catalyzes the cross-linking of polypeptide chains (glutamine and lysine residues in substrate proteins)—including ECM related proteins (Johnson et al, *J. Clin. Invest.* 99(12):2950–2960 (1997)). Also, chondrocyte hypertrophy results in an increase in TGase (Nurminskaya & Linsenmayer, *Dev. Dyn.* 206(3):260–271 (1996)). TGase binds and covalently cross-links fibronectin—and thereby is involved in cellular adhesion, tissue organization, and wound repair (Achyuthan et al, *J. immuno. Methods* 180(l):69–79 (1995)).

A component of adhesion plaques, zyxin (ZN) is involved in the microfilament organization within focal contact sites and is found primarily in cyto-skeleton associated fibroblasts. Reinhard et al, *FEBS Lett.* 399(1–2):103–107 (1996) found that the vasodilator-stimulated phosphoprotein (VASP) acts as a ligand for both profilin and zyxin (both involved in the adherins junctions). Although the putative designation of ZN as an attachment protein to the ECM is substantiated by numerous protein interaction studies, there are two important deviations in the amino acid structure and sequence of ZN compared to other adherin-associated proteins: 1) the amino acid sequence of ZN displays a high degree of similarity with proto-oncogenic products and transcriptional regulators (Schmeichel & Beckerle, *Mol. Biol. Cell* 8(2 :219–230 (1994)), and 2) there are three distinct LIM domains in ZN which are involved in metal binding (Macalma et al., *J. Biol. Chem.* 271(49):31470–31478 (1996)).

It should be noted that citation or discussion of a reference herein shall not be construed as an admission that such is prior art to the present invention.

SUMMARY OF THE INVENTION

The present inventors have applied quantitative expression analysis to a rat surgical model of cardiac hypertrophy (RCH) which produces a 60% increase in ventricle mass. The present inventors discovered that, of the 12,000 QEA-generated gene fragments derived from approximately 6,000 genes, 39 fragments (0.3%) were found to be differentially expressed in the hypertrophic hearts relative to controls. The present inventors further discovered that the expression level of a number of genes, not previously associated with cardiac hypertrophy, is significantly altered in the surgical model of cardiac hypertrophy. Expression of genes with homology to short-chain alcohol dehydrogenase, Desmin, Protein Kinase C-Binding Protein β15 and genes encoding 5.8S, 18S and 28S rRNAs are inhibited, while the expression of genes with homology to mouse α-1 Collagen Type III, mouse α-1 Collagen Type IV, chicken Collagen Type XIV, human 13kD DAP, mouse and human Gelsolin, mouse Osteonectin, mouse Transglutaminase, and mouse and human Zyxin, as well as the α-Enolase, Antizyme Inhibitor, Biglycan, Cytochrome Oxidase I, Cytochrome Oxidase II, Cyclin G, Rat D-binding protein, Fibrillin, Laminin γ-1, p85 and Preproenkephalin genes is induced in the cardiac hypertrophy model. The above-listed genes, both the induced and inhibited genes, are collectively referred to as cardiac hypertrophy associated gene ("CHAG" hereinafter). Accordingly, these identified CHAG genes, RNA and proteins encoded by CHAG genes are useful in the treatment and prevention of cardiac hypertrophy, and screening for predisposition to or for protection against cardiac hypertrophy.

The present invention further relates to nucleotide sequences of CH-1, CH-2, CH-3, CH-4, CH-5, CH-6, CH-7, CH-8 and CH-9 genes, which have nucleotide sequence homology to human short-chain alcohol dehydrogenase and mouse amyloid beta-peptide binding protein, to mouse α-1 Collagen Type III, to mouse α-1Collagen Type IV, to chicken Collagen Type XIV, to human 13kD DAP, to mouse and human Gelsolin, to mouse Osteonectin, to mouse Transglutaminase, and mouse and human Zyxin, respectively. The present inventors have found that these genes are differentially expressed in hypertropic cardiac tissue as compared to normal cardiac tissue. Accordingly, the present invention relates to nucleotide sequences of CH-1, CH-2, CH-3, CH-4, CH-5, CH-6, CH-7, CH-8 and CH-9, and amino acid sequences of their encoded proteins, as well as derivatives (e.g., fragments) and analogs thereof. Nucleic acids hybridizable, or complementary, or in particular, inversely complementary to the foregoing nucleotide sequences are also provided. In a specific embodiment, the above-listed proteins are human proteins.

The invention also relates to derivatives (including fragments) and analogs of CH-1, CH-2, CH-3, CH-4, CH-5, CH-6, CH-7, CH-8 and CH-9 proteins which are functionally active, i.e., they are capable of displaying one or more known functional activities associated with a full-length (wild-type) protein. Such functional activities include but are not limited to antigenicity [ability to bind (or compete with the above-listed proteins for binding) to an antibody against the above-listed proteins], and immunogenicity (ability to generate antibody which binds to the above-listed proteins).

Antibodies to the above-listed proteins, and derivatives and analogs thereof, are additionally provided.

Methods of production of the proteins encoded by CH-1, CH-2, CH-3, CH-4, CH-5, CH-6, CH-7, CH-8 and CH-9, and derivatives and analogs thereof, e g., by recombinant means, are also provided.

The present invention further relates to therapeutic and diagnostic methods, particularly methods of treating, preventing, diagnosing or screening for cardiac hypertrophy, and compositions based on CHAG (CH-1, CH-2, CH-3, CH-4, CH-5, CH-6, CH-7, CH-8, CH-9, and α-Enolase, Antizyme Inhibitor, Biglycan, Cytochrome Oxidase I, Cytochrome Oxidase II, Cyclin G, D-binding protein, Desmin, Fibrillin, Laminin γ-1, p85, Preproenkephalin, Protein Kinase C-Binding Protein β15, and genes encoding 5.8S, 18S and 28S rRNAs) proteins and nucleic acids. Therapeutic compounds of the invention include but are not limited to CHAG proteins and analogs and derivatives (including fragments) thereof; anti-CHAG antibodies; nucleic acids encoding the CHAG proteins, analogs, or derivatives; and CHAG antisense nucleic acids.

Animal models and methods to identify agonists and antagonists of CHAG are also provided by the invention.

(I) Definitions

CHAG: cardiac hypertrophy associated genes, identified by the present inventors, including CH-1, CH-2, CH-3, CH-4, CH-5, CH-6, CH-7, CH-8, CH-9, and α-Enolase, Antizyme Inhibitor, Biglycan, Cytochrome Oxidase I, Cytochrome Oxidase II, Cyclin G, D-binding protein, Desmin, Fibrillin, Laminin γ-1, p85 and Preproenkephalin, Protein Kinase C-Binding Protein β15 and genes encoding 5.8S, 18S and 28S rRNAs.

CH: novel cardiac hypertrophy genes including: CH-1, CH-2, CH-3, CH-4, CH-5, CH-6, CH-7, CH-8 and CH-9.

QEA®: Quantitative Expression Analysis.

DESCRIPTION OF THE FIGURES

In order that the present invention disclosed herein is better understood and appreciated, the following detailed description is set forth.

FIG. 2 is a depiction of: (Panel A) the complementary nucleotide sequence to CH-1 [SEQ ID NO:1], (Panel B) a comparison of Query sequence CH-1 [SEQ ID NO:10] with the Sbjct ("subject") nucleotide sequence of the mouse amyloid beta-peptide binding protein [SEQ ID NO:11], and (Panel C) a comparison of Query sequence CH-1 [SEQ ID NO:12] with the Sbjct ("subject") nucleotide sequence of the human short-chain alcohol dehydrogenase [SEQ ID NO:13].

FIG. 3 is a depiction of: (Panel A) the complementary nucleotide sequence to CH-2 [SEQ ID NO:2], and (Panel B) a comparison of Query sequence CH-2 [SEQ ID NO:14] with the Sbjct ("subject") nucleotide sequence of mouse α-1 Collagen Type III [SEQ ID NO:15].

FIG. 4 is a depiction of: (Panel A) the complementary nucleotide sequence to CH-3 [SEQ ID NO:3] and (Panel B) a comparison of Query sequence CH-3 [SEQ ID NO:16] with the Sbjct (subject) nucleotide sequence of mouse α-1 Collagen Type IV [SEQ ID NO:17]. The internal sequence identifies consensus nucleotides between the two sequences [SEQ ID NO:18].

FIG. 5 is a depiction of: (Panel A) the nucleotide sequence of CH-4 [SEQ ID NO:4], and (Panel B) a comparison of Query sequence CH-4 [SEQ ID NO:4] with the Sbjct ("subject") nucleotide sequence of human Collagen Type XIV [SEQ ID NO:19].

FIG. 6 is a depiction of: (Panel A) the nucleotide sequence of CH-5 [SEQ ID NO:5], and (Panel B) a comparison of Query sequence CH-5 [SEQ ID NO:20] with the Sbjct ("subject") nucleotide sequence of human 13kD DAP [SEQ ID NO:21] The internal sequence identifies consensus nucleotides between the two sequences [SEQ ID NO:22].

FIG. 7 is a depiction of: (Panel A) the complementary nucleotide sequence to CH-6 [SEQ ID NO:6], and (Panel B) a comparison of Query sequence CH-6 [SEQ ID NO:23] with the Sbjct ("subject") nucleotide sequence of mouse Gelsolin [SEQ ID NO:24] The internal sequence identifies consensus nucleotides between the two sequences [SEQ ID NO:25].

FIG. 8 is a depiction of: (Panel A) the nucleotide sequence of CH-7 [SEQ ID NO:7], and (Panel B) a comparison of Query sequence CH-7 [SEQ ID NO:7] with the Sbjct ("subject") nucleotide sequence of rat Osteonectin [SEQ ID NO:26].

FIG. 9 is a depiction of: (Panel A) the complementary nucleotide sequence to CH-8 [SEQ ID NO:8], and (Panel B) a comparison of Query sequence CH-8 [SEQ ID NO:27] with the Sbjct ("subject") nucleotide sequence of mouse Transglutaminase [SEQ ID NO:28]. The internal sequence identifies consensus nucleotides between the two sequences [SEQ ID NO:29].

FIG. 10 is a depiction of: (Panel A) the complementary nucleotide sequence to CH-9 [SEQ ID NO:9], and (Panel B) a comparison of Query sequence CH-9 [SEQ ID NO:30] with the Sbjct ("subject") nucleotide sequence of mouse Zyxin [SEQ ID NO:31]. The internal sequence identifies consensus nucleotides between the two sequences [SEQ ID NO:32].

DETAILED DESCRIPTION OF THE INVENTION

Figure 1:
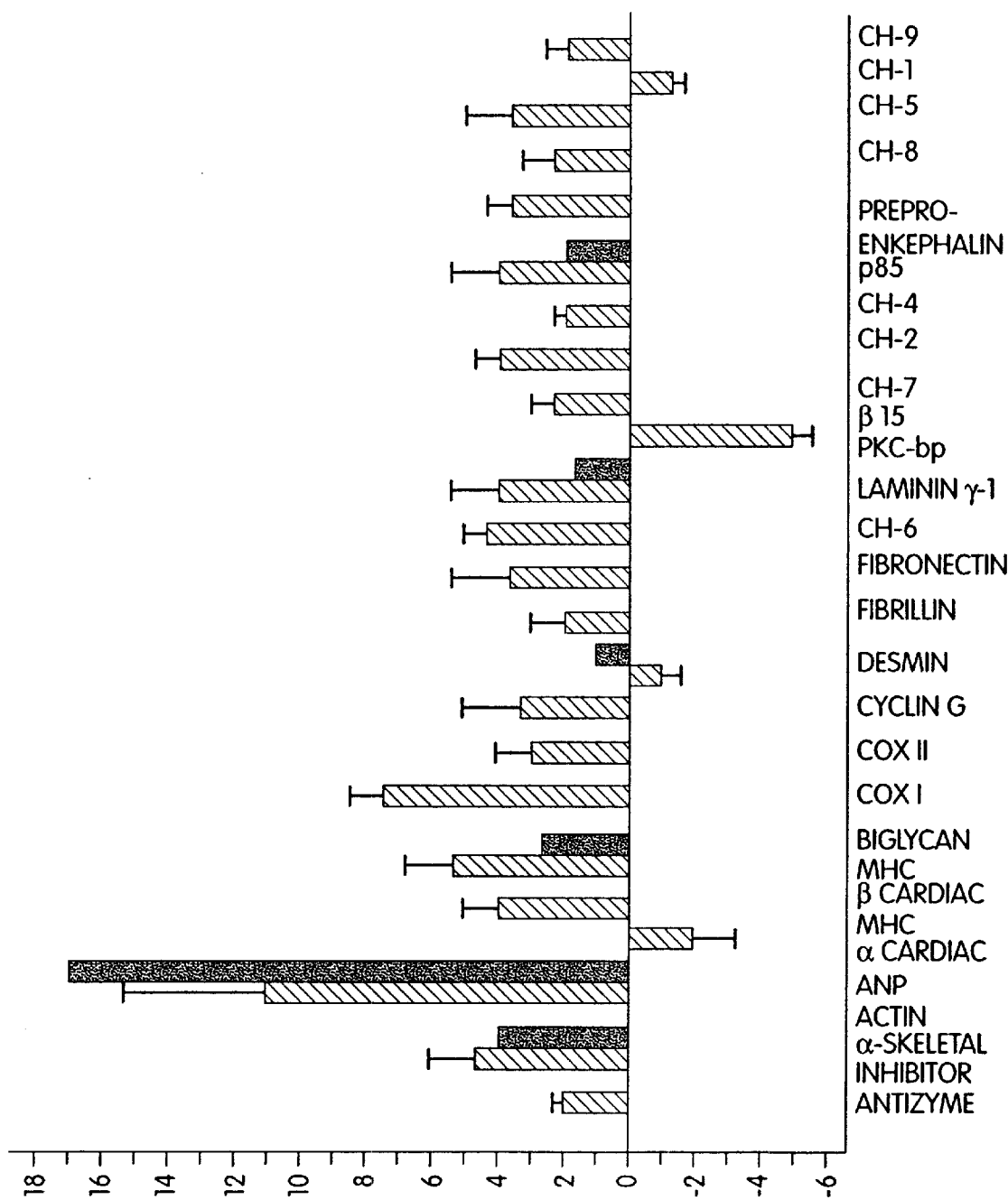
FIG. 1 depicts gene expression assayed by QEA and Northern analysis. Twenty two genes were identified by QEA as being differentially expressed in Pressure Overload (POL) hearts. The graph depicts the relative increase (+values) or decrease (-values) in levels of gene expression averaged between the POL and unoperated hearts and the POL and sham operated hearts. Gray bars indicate the relative expression values as determined by QEA, black bars indicate the relative expression values as determined by Northern analysis.

The present inventors have applied quantitative expression analysis to a rat surgical model of cardiac hypertrophy (RCH) which results in a 60% increase in ventricle mass. The present inventors discovered that the expression level of a number of known genes, not previously associated with cardiac hypertrophy, is significantly altered in the surgical model of cardiac hypertrophy. The inventors have also identified nine novel genes, defined as CH-1, CH-2, CH-3, CH-4, CH-5, CH-6, CH-7, CH-8, and CH-9, that have nucleotide sequence homology to, but are not identical to, the human short-chain alcohol dehydrogenase and mouse amyloid beta-peptide binding protein, mouse α-1 Collagen Type III, mouse α-1 Collagen Type IV, chicken Collagen Type XIV, human 13kD DAP, mouse and human Gelsolin, mouse Osteonectin, mouse Transglutaminase, and mouse and human Zyxin, respectively. Other genes identified in the present invention include α-Enolase, Antizyme Inhibitor, Biglycan, Cytochrome Oxidase I, Cytochrome Oxidase II, Cyclin G, Rat D-binding protein, Desmin, Fibrillin, Laminin α-1, p85, Preproenkephalin, Protein Kinase C-Binding Protein β15 and genes encoding 5.8S, 18S and 28S rRNAs. CH-1, Desmin, Protein Kinase C-Binding Protein β15 and genes encoding 5.8S, 18S and 28S rRNAs are down-regulated in hypertrophic cardiac tissues compared to controls. CH-2, CH-3, CH-4, CH-5, CH-6, CH-7, CH-8, CH-9, and α-Enolase, Antizyme Inhibitor, Biglycan, Cytochrome Oxidase I, Cytochrome Oxidase II, Cyclin G, Rat D-binding protein, Fibrillin, Laminin α-1, p85 and Preproenkephalin are up-regulated in hypertrophic cardiac tissues compared to controls.

Accordingly, the present invention provides the nucleotide sequences of CH-1, CH-2, CH-3, CH-4, CH-5, CH-6, CH-7, CH-8, and CH-9, and the amino acid sequence of the proteins encoded by these genes. The invention further relates to the proteins, derivatives, fragments and homologs thereof, as well as nucleic acids encoding the above-listed proteins, derivatives, fragments and homologs. The invention provides the above-listed proteins and genes encoding these proteins of many different species, particularly vertebrates, and more particularly mammals. In a preferred embodiment, the above-listed proteins and genes are of human origin. Production of the foregoing proteins and derivatives, e.g., by recombinant methods, is provided.

The invention also provides derivatives and analogs of the above-listed proteins which are functionally active, i.e., capable of displaying one or more known functional activities associated with a full length (wild-type) protein selected from the group consisting of the above-listed proteins. Such functional activities include, but are not limited to, antigenicity [ability to bind (or compete with the above-listed proteins for binding) to an antibody to the above-listed proteins, respectively], immunogenicity (ability to generate an antibody that binds to the above-listed proteins), etc.

Antibodies to proteins encoded by CH-1, CH-2, CH-3, CH-4, CH-5, CH-6, CH-7, CH-8, and CH-9, and derivatives and analogs thereof, are additionally provided.

The present invention further relates to therapeutic and diagnostic methods and compositions based on CHAG proteins and nucleic acids. The invention provides for treatment of cardiac hypertrophy by administering compounds that modulate (i.e. promote, antagonize or inhibit) CHAG protein activity (e.g, CHAG proteins and functionally active analogs and derivatives (including fragments) thereof, nucleic acids encoding the CHAG proteins, analogs, or derivatives, agonists of CHAG proteins).

Animal models, diagnostic methods and screening methods for predisposition to cardiac hypertrophy are also provided by the invention.

For clarity of disclosure, and not by way of limitation, the detailed description of the invention is divided into the subsections which follow.

(1) CHAG Proteins and Derivatives and Analogs

The invention relates to CHAG proteins as well as derivatives (including but not limited to fragments) and homologs and paralogs of CHAG proteins. In one embodiment human CHAG genes and proteins are provided. In specific aspects, the native proteins, fragments, derivatives or analogs of CHAG are of animals, e.g mouse, rat, chicken, or human. In other specific embodiments, the fragment, derivative or analog is functionally active, i.e., capable of exhibiting one or more functional activities associated with full-length, wild-type CHAG, e.g., immunogenicity or antigenicity.

The nucleotide sequences encoding, and the corresponding amino acid sequences, of rat α-Enolase (GenBank Accession No. H35207), Antizyme Inhibitor (GenBank Accession No. D50734), Biglycan (GenBank Accession No. U17834), Cytochrome Oxidase I (GenBank Accession No. J01435), Cytochrome Oxidase II (GenBank Accession No. J01434), Cyclin G (GenBank Accession No. X7087 1), D-binding protein (GenBank Accession No. J03179), Desmin GenBank Accession No. X73524), Fibrillin (GenBank Accession No. L19896), Laminin γ-1 (GenBank Accession No. X94551), Protein kinase C-binding protein β 15 (GenBank Accession No. U48248), p85 (GenBank Accession No. U42581), 5.8S–18S–28S rRNAs (GenBank Accession No. V01272), Preproenkephalin (GenBank Accession No. K02805), and human 28S rRNA (GenBank Accession No. M11167), are known. Partial nucleic acid sequences of CH-1, CH-2, CH-3, CH-4, CH-5, CH-6, CH-7, CH-8, and CH-9 are disclosed in FIGS. 2–10, Panels A and Query sequences of Panels B and C, respectively. Complete nucleic acids of CH-1, CH-2, CH-3, CH-4, CH-5, CH-6, CH-7, CH-8, and CH-9 can be obtained by any method known in the art, e.g., by PCR amplification using synthetic primers hybridizable to the 3' and 5' ends of the sequence and/or by cloning from a cDNA or genomic library using a PCR amplification product or an oligonucleotide specific for the gene sequence (e.g., as described in Section 5.2, infra). Homologs (e.g., nucleic acids of the above-listed genes of species other than rat) or other related sequences (e.g., paralogs) can be obtained by low, moderate or high stringency hybridization with all or a portion of the particular sequence provided as a probe using methods well known in the art for nucleic acid hybridization and cloning (e.g., as described in Section 5.2, infra, for nucleic acids of CH-1, CH-2, CH-3, CH-4, CH-5, CH-6, CH-7, CH-8, and CH-9).

The CHAG proteins can be obtained by methods well known in the art for protein purification and recombinant protein expression. For recombinant expression of one or more of the proteins, the nucleic acid containing all or a portion of the nucleotide sequence encoding the protein can be inserted into an appropriate expression vector, i.e., a vector that contains the necessary elements for the transcription and translation of the inserted protein coding sequence. The necessary transcriptional and translational signals can also be supplied by the native promoter for CHAG genes, and/or their flanking regions.

A variety of host-vector systems may be utilized to express the protein coding sequence. These include but are not limited to mammalian cell systems infected with virus (e.g. vaccinia virus, adenovirus, etc.); insect cell systems infected with virus (e.g. baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Any of the methods described in Section 5.2 infra, for the insertion of DNA fragments into a vector may be used to construct expression vectors containing a chimeric gene consisting of appropriate transcriptional/translational control signals and protein coding sequences. These methods may include in vitro recombinant DNA and synthetic techniques and in vivo recombinants (genetic recombination). Expression of nucleic acid sequences encoding CHAG, or derivatives, fragments or homologs thereof, may be regulated by a second nucleic acid sequence so that the genes or fragments thereof are expressed in a host transformed with the recombinant DNA molecule(s). For example, expression of the proteins may be controlled by any promoter/enhancer known in the art. In a specific embodiment, the promoter is not native to the genes for CHAG. Promoters which may be used include but are not limited to the SV40 early promoter (Bernoist and Chambon, Nature 290:304–310 (1981)), the promoter contained in the 3'-long terminal repeat (LTR) of Rous sarcoma virus (Yamamoto et al., Cell 22:787–797 (1980)), the herpes thymidine kinase promoter (Wagner et al., Proc. Natl. Acad. Sci. USA 78:1441–1445 (1981)), the regulatory sequences of the metallothionein gene (Brinster et al., Nature 296:39–42 (1982)); prokaryotic expression vectors such as the β-lactamase promoter (Villa-Kamaroffet al., Proc. Natl. Acad. Sci. USA 75:3727–3731 1978)) or the tac promoter (DeBoer et al., Proc. Natl. Acad. Sci. USA 80:21–25 (1983)); see also AUseful Proteins from Recombinant Bacteria: in Scientific American 242:79–94 (1980)); plant expression vectors comprising the nopaline synthetase promoter (Herrar-Estrella et al., *Nature* 303:209–213 (1984)) or the cauliflower mosaic virus 35S RNA promoter (Garder et al., *Nucleic Acids Res.* 9:2871 (1981)), and the promoter of the photosynthetic enzyme ribulose bisphosphate carboxylase (Herrera-Estrella et al., *Nature* 310:115–120 (1984)); promoter elements from yeast and other fungi such as the Gal4 promoter, the alcohol dehydrogenase promoter, the phosphoglycerol kinase promoter, the alkaline phosphatase promoter, and the following animal transcriptional control regions that exhibit tissue specificity and have been utilized in transgenic animals: elastase I gene control region which is active in pancreatic acinar cells (Swift et al., *Cell* 38:639–646 (1984); Ornitz et al., *Cold Spring Harbor Symp. Quant. Biol.* 50:399–409 (1986); MacDonald, *Hepatology* 7:425–515 (1987)); insulin gene control region which is active in pancreatic beta cells (Hanahan et al., *Nature* 315:115–122 (1985)), immunoglobulin gene control region which is active in lymphoid cells (Grosschedl et al., *Cell* 38:647–658 (1984); Adams et al., *Nature* 318:533–538 (1985); Alexander et al., *Mol. Cell Biol.* 7:1436–1444 (1987)), mouse mammary tumor virus control region which is active in testicular, breast, lymphoid and mast cells (Leder et al., *Cell* 45:485–495 (1986)), albumin gene control region which is active in liver (Pinckert et al., *Genes and Devel.* 1:268–276 (1987)), alpha-fetoprotein gene control region which is active in liver (Krumlauf et al., *Mol. Cell. Biol.* 5:1639–1648 (1985); Hammer et al., *Science* 235:53–58 1987)), α-1 antitrypsin gene control region which is active in liver (Kelsey et al., *Genes and Devel.* 1:161–171 (1987)), beta globin gene control region which is active in myeloid cells (Mogram et al., *Nature* 315:338–340 (1985); Kollias et al., *Cell* 46:89–94 (1986)), myelin basic protein gene control region which is active in oligodendrocyte cells of the brain (Readhead et al., *Cell* 48:703–712 (1987)), myosin light chain-2 gene control region which is active in skeletal muscle (Sani, *Nature* 314:283–286 (1985)), and gonadotrophic releasing hormone gene control region which is active in gonadotrophs of the hypothalamus (Mason et al., *Science* 234:1372–1378 (1986)).

In a specific embodiment, a vector is used that comprises a promoter operably linked to nucleic acid sequences encoding CHAG, or a fragment, derivative or homolog, thereof, one or more origins of replication, and optionally, one or more selectable markers (e.g., an antibiotic resistance gene).

In another specific embodiment, an expression vector containing the coding sequences, or portions thereof, of CHAG, is made by subcloning the gene sequences into the EcoRI restriction site of each of the three pGEX vectors (glutathione S-transferase expression vectors (Smith and Johnson, *Gene* 7:31–40 (1988)). This allows for the expression of gene products in the correct reading frame.

Expression vectors containing the sequences of interest can be identified by three general approaches: (a) nucleic acid hybridization, (b) presence or absence of a marker of gene function, and (c) expression of the inserted sequences. In the first approach, CHAG sequences can be detected by nucleic acid hybridization to probes comprising sequences homologous and complementary to the inserted sequences. In the second approach, the recombinant vector/host system can be identified and selected based upon the presence or absence of certain marker functions (e.g., binding to an anti-CHAG antibody, resistance to antibiotics, occlusion body formation in baculovirus, etc.) caused by insertion of the sequences of interest in the vector. For example, if a CHAG gene, or portion thereof, is inserted within the marker gene sequence of the vector, recombinants containing the CHAG fragment will be identified by the absence of the marker gene function. In the third approach, recombinant expression vectors can be identified by assaying for the CHAG, or other CHAG products expressed by the recombinant vector. Such assays can be based, for example, on the physical or functional properties of the interacting species in in vitro assay systems, e.g., activation of T cell, immunoreactivity to antibodies specific for the protein.

Once recombinant CHAG molecules are identified and the proteins isolated, several methods known in the art can be used to propagate them. Once a suitable host system and growth conditions have been established, recombinant expression vectors can be propagated and amplified in quantity. As previously described, the expression vectors or derivatives which can be used include, but are not limited to: human or animal viruses such as vaccinia virus or adenovirus; insect viruses such as baculovirus, yeast vectors; bacteriophage vectors such as lambda phage; and plasmid and cosmid vectors.

In addition, a host cell strain may be chosen that modulates the expression of the inserted sequences, or modifies or processes the expressed proteins in the specific fashion desired. Expression from certain promoters can be elevated in the presence of certain inducers; thus expression of the genetically-engineered CHAG may be controlled. Furthermore, different host cells have characteristic and specific mechanisms for the translational and post-translational processing and modification (e.g. glycosylation, phosphorylation, etc.) of proteins. Appropriate cell lines or host systems can be chosen to ensure the desired modification and processing of the foreign protein is achieved. For example, expression in a bacterial system can be used to produce an unglycosylated core protein, while expression in mammalian cells ensures native glycosylation of a heterologous protein. Furthermore, different vector/host expression systems may effect processing reactions to different extent.

In other specific embodiments, the CHAG or fragments, homologs or derivatives thereof, may be expressed as fusion or chimeric protein products comprising the protein, fragment, homolog, or derivative joined via a peptide bond to a heterologous protein sequence of a different protein. Such chimeric products can be made by ligating the appropriate nucleic acid sequences encoding the desired amino acids to each other by methods known in the art, in the proper coding frame, and expressing the chimeric products in a suitable host by methods commonly known in the art. Alternatively, such a chimeric product can be made by protein synthetic techniques, e.g., by use of a peptide synthesizer. Chimeric genes comprising portions of CHAG fused to any heterologous protein-encoding sequences may be constructed. A specific embodiment relates to a chimeric protein comprising a fragment of CHAG of at least 6 amino acids.

In particular, CHAG derivatives can be made by altering their sequences by substitutions, additions or deletions that provide for functionally equivalent molecules. Due to the degeneracy of nucleotide coding sequences, other DNA sequences which encode substantially the same amino acid sequence as a CHAG gene can be used in the practice of the present invention. These include but are not limited to nucleotide sequences comprising all or portions of CHAG genes that are altered by the substitution of different codons that encode the amino acid residue within the sequence, thus producing a silent change. Likewise, the CHAG derivatives of the invention include, but are not limited to, those containing, as a primary amino acid sequence, all or part of the amino acid sequence of CHAG, including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In a specific embodiment of the invention, the nucleic acids encoding proteins and proteins consisting of or comprising a fragment of CHAG consisting of at least 6 (continuous) amino acids of CHAG are provided. In other embodiments, the fragment consists of at least 10, 20, 30, 40, or 50 amino acids of CHAG. In specific embodiments, such fragments are not larger than 35, 100 or 200 amino acids. Derivatives or analogs of CHAG include but are not limited to molecules comprising regions that are substantially homologous to CHAG in various embodiments, at least 30%, 40%, 50%, 60%, 70%, 80%, 90% or 95% identity over an amino acid sequence of identical size or when compared to an aligned sequence in which the alignment is done by a computer homology program known in the art or whose encoding nucleic acid is capable of hybridizing to a sequence encoding CHAG under stringent, moderately-stringent, or non-stringent conditions.

The CHAG derivatives and analogs of the invention can be produced by various methods known in the art. The manipulations which result in their production can occur at the gene or protein level. For example, the cloned CHAG gene sequence can be modified by any of numerous strategies known in the art (Sambrook et al., 1990*, Molecular Cloning, A Laboratory Manual*, 2d ed., Cold Spring Harbor Laboratory, Cold Spring Harbor, N.Y.). The sequences can be cleaved at appropriate sites with restriction endonuclease (s), followed by further enzymatic modification if desired, isolated, and ligated in vitro. In the production of the gene encoding a derivative or analog of CHAG, care should be taken to ensure that the modified gene retains the original translational reading frame, uninterrupted by translational stop signals, in the gene region where the desired activity is encoded.

Additionally, the CHAG-encoding nucleotide sequence can be mutated in vitro or in vivo, to create and/or destroy translation, initiation; and/or termination sequences, or to create variations in coding regions and/or form new restriction endonuclease sites or destroy pre-existing ones, to facilitate further in vitro modification. Any technique for mutagenesis known in the art can be used, including but not limited to, chemical mutagenesis and in vitro site-directed mutagenesis (Hutchinson et al., *J. Biol. Chem.* 253:6551–6558 (1978)), use of TAB7 linkers (Pharmacia), etc.

Once a recombinant cell expressing a CHAG protein, or fragment or derivative thereof, is identified, the individual gene product can be isolated and analyzed. This is achieved by assays based on the physical and/or functional properties of the protein, including, but not limited to, radioactive labeling of the product followed by analysis by gel electrophoresis, immunoassay, cross-linking to marker-labeled product, etc.

The CHAG proteins may be isolated and purified by standard methods known in the art (either from natural sources or recombinant host cells expressing the complexes or proteins), including but not restricted to column chromatography (e.g., ion exchange, affinity, gel exclusion, reversed-phase high pressure, fast protein liquid, etc.), differential centrifugation, differential solubility, or by any other standard technique used for the purification of proteins. Functional properties may be evaluated using any suitable assay known in the art.

Alternatively, once a CHAG or its derivative is identified, the amino acid sequence of the protein can be deduced from the nucleotide sequence of the gene which encodes it. As a result, the protein or its derivative can be synthesized by standard chemical methods known in the art (e.g. see Hunkapiller et al, *Nature* 310:105–111 (1984)).

Manipulations of CHAG sequences may be made at the protein level. Included within the scope of the invention are CHAG derivatives or analogs or fragments, which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

In specific embodiments, the CHAG sequences are modified to include a fluorescent label. In another specific embodiment the CHAG is modified to have a heterofunctional reagent, such heterofunctional reagents can be used to cross-link the members of the complex.

In addition, analogs and derivatives of a CHAG can be chemically synthesized. For example, a peptide corresponding to a portion of a CHAG, which comprises the desired domain or which mediates the desired activity in vitro can be synthesized by use of a peptide synthesizer. Furthermore, if desired, non-classical amino acids or chemical amino acid analogs can be introduced as a substitution or addition into the CHAG sequence. Non-classical amino acids include, but are not limited to the D-isomers of the common amino acids, a-amino isobutyric acid, 4-aminobutyric acid, Abu, 2-aminobutyric acid, α-Abu, ε-Ahx, 6-amino hexanoic acid, Aib, 2-amino isobutyric acid, 3-amino propionoic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Ca-methyl amino acids, Na-methyl amino acids, and amino acid analogs in general.

In cases where natural products are suspected of being mutant or are isolated from new species, the amino acid sequence of the CHAG isolated from the natural source, as well as those expressed in vitro, or from synthesized expression vectors in vivo or in vitro, can be determined from analysis of the DNA sequence, or alternatively, by direct sequencing of the isolated protein. Such analysis may be performed by manual sequencing or through use of an automated amino acid sequenator.

The CHAG proteins may also be analyzed by hydrophilicity analysis (Hopp and Woods, *Proc. Nail. Acad. Sci. USA*

78:3824–3828 (1981)). A hydrophilicity profile can be used to identify the hydrophobic and hydrophilic regions of the proteins, and help predict their orientation in designing substrates for experimental manipulation, such as in binding experiments, antibody synthesis, etc. Secondary structural analysis can also be done to identify regions of the CHAG that assume specific structures (Chou and Fasman, *Biochemistry* 13:222–23 (1974)). Manipulation, translation, secondary structure prediction, hydrophilicity and hydrophobicity profiles, open reading frame prediction and plotting, and determination of sequence homologies, can be accomplished using computer software programs available within the art.

Other methods of structural analysis including but not limited to X-ray crystallography (Engstrom, *Biochem. Exp. Biol.* 11:7–13 (1974)), mass spectroscopy and gas chromatography (Methods in Protein Science, J. Wiley and Sons, New York, 1997), and computer modeling (Fletterick and Zoller, eds., 1986, Computer Graphics and Molecular Modeling, In: *Current Communications in Molecular Biology*, Cold Spring Harbor Laboratory, Cold Spring Harbor Press, New York) can also be employed.

(2) Identification and Isolation of CH Genes

The invention relates to the nucleotide sequences of CH-1, CH-2, CH-3, CH-4, CH-5, CH-6, CH-7, CH-8, and CH-9. In specific embodiments, the CH nucleic acids comprise the sequence of SEQ ID NOS:1–9 respectively, (as depicted in FIGS. 2A–10A, respectively) or the coding regions thereof, or nucleotide sequences encoding, in whole or in part, a CH protein (as depicated in FIG. 2–20). The invention provides purified nucleic acids consisting of at least 8 nucleotides (i.e., a hybridizable portion) of a CH sequence; in other embodiments, the nucleic acids consist of at least 25 (continuous) nucleotides, 50 nucleotides, 100 nucleotides, 150 nucleotides, or 200 nucleotides of a CH sequence, or a full-length CH coding sequence. In another embodiment, the nucleic acids are smaller than 35, 200 or 500 nucleotides in length. Nucleic acids can be single or double stranded. The invention also relates to nucleic acids hybridizable to or complementary to the foregoing sequences, in particular the invention provides the inverse complement to nucleic acids hybridizable to the foregoing sequences (i.e. the inverse complement of a nucleic acid strand has the complementary sequence running in reverse orientation to the strand so that the inverse complement would hybridize without mismatches to the nucleic acid strand; thus, for example, where the coding strand is hybridizable to a nucleic acid with no mismatches between the coding strand and the hybridizable strand, then the inverse complement of the hybridizable strand is identical to the coding strand). In specific aspects, nucleic acids are provided which comprise a sequence complementary to (specifically are the inverse complement of) at least 10, 25, 50, 100, or 200 nucleotides or the entire coding region of a CH gene.

In a specific embodiment, a nucleic acid which is hybridizable to a CH nucleic acid (e.g., having a sequence of SEQ ID NOS:1–9, respectively), or to a nucleic acid encoding a CH derivative, under conditions of low stringency is provided. By way of example and not limitation, procedures using such conditions of low stringency are as follows (see also Shilo and Weinberg, *Proc. Natl. Acad. Sci. USA* 78:6789–6792 (1981)): Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe is used. Filters are incubated in hybridization mixture for 18–20 hours at 40° C., and then washed for 1.5 hours at 55° C. in a solution containing 2×SSC; 25 mM Tris-HCl (pH 7.4), 5 mM EDTA, and 0.1% SDS. The wash solution is replaced with fresh solution and incubated an additional 1.5 hours at 60° C. Filters are blotted dry and exposed for autoradiography. If necessary, filters are washed for a third time at 65–68° C. and re-exposed to film. Other conditions of low stringency which may be used are well known in the art (e.g., as employed for cross-species hybridizations).

In another specific embodiment, a nucleic acid which is hybridizable to a CH nucleic acid under conditions of high stringency is provided. By way of example and not way of limitation, procedures using such conditions of high stringency are as follows: Prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 hours at 65EC in prehybridization mixture containing 100 µg/ml denatured salmon sperm DNA and 5–20×10$^6$ cpm of $^{32}$P-labeled probe. Washing of filters is done at 37° C. for 1 hour in a solution containing 2×SSC, 0.01% PVP, 0.01% Ficoll, and 0.01% BSA. This is followed by a wash in 0.1×SSC at 50° C. for 45 minutes before autoradiography. Other conditions of high stringency which may be used are well-known within the art.

In another specific embodiment, a nucleic acid, which is hybridizable to a CH nucleic acid under conditions of moderate stringency is provided. For example, but not limited to, procedures using such conditions of moderate stringency are as follows: Filters containing DNA are pretreated for 6 hours at 55° C. in a solution containing 6×SSC, 5×Denhart's solution, 0.5% SDS and 100 µg/ml denatured salmon sperm DNA. Hybridizations are carried out in the same solution and 5–20×10$^6$ cpm $^{32}$P-labeled probe is used. Filters are incubated in hybridization mixture for 18–20 hours at 55° C., and then washed twice for 30 minutes at 60° C. in a solution containing 1×SSC and 0.1% SDS. Filters are blotted dry and exposed for autoradiography. Other conditions of moderate stringency which may be used are well-known in the art. Washing of filters is done at 37° C. for 1 hour in a solution containing 2×SSC, 0.1% SDS.

Nucleic acids encoding derivatives and analogs of CH proteins and CH antisense nucleic acids are additionally provided. As is readily apparent, as used herein, a "nucleic acid encoding a fragment or portion of a CH" shall be construed as referring to a nucleic acid encoding only the recited fragment or portion of CH protein, and not the other contiguous portions of the CH as a continuous sequence.

Fragments of CH nucleic acids comprising regions conserved between (with homology to) other CH nucleic acids, of the same or different species, are also provided.

Any method available in the art can be used to obtain a full length (i.e., encompassing the entire coding region) cDNA or genomic DNA clone encoding a CH. In particular, the polymerase chain reaction (PCR) can be used to amplify a sequence identified as being differentially expressed in hypertrophic cardiac tissue, e.g. nucleic acids comprising the nucleotide sequences of CH-1, CH-2, CH-3, CH-4, CH-5, CH-6, CH-7, CH-8 and CH-9 (SEQ. NOS: 1–9 respectively), in a genomic or cDNA library. Oligonucleotide primers that hybridize to sequences at the 3'- and 5'-termini of the identified sequences can be used as primers to amplify by PCR sequences from a nucleic acid sample (RNA or DNA), preferably a cDNA library, from an appropriate source (e.g. hypertrophic cardiac tissue).

PCR can be carried out, e.g., by use of a Perkin-Elmer Cetus thermal cycler and Taq polymerase (Gene Amp®). The DNA being amplified can include mRNA or cDNA or genomic DNA from any eukaryotic species. One can choose to synthesize several different degenerate primers, for use in the PCR reactions. It is also possible to vary the stringency of hybridization conditions used in priming the PCR reactions, to amplify nucleic acid homologs (e.g., to obtain CH sequences from species other than humans or to obtain human sequences with homology to CH) by allowing for greater or lesser degrees of nucleotide sequence similarity between the known nucleotide sequence and the nucleic acid homolog being isolated. For cross species hybridization, low stringency conditions are preferred. For same species hybridization, moderately stringent conditions are preferred.

After successful amplification of the nucleic acid containing all or a portion of the identified CH sequence or of a nucleic acid encoding all or a portion of a CH homolog, that segment may be molecularly cloned and sequenced, and utilized as a probe to isolate a complete cDNA or genomic clone. This, in turn, will permit the determination of the gene's complete nucleotide sequence, the analysis of its expression, and the production of its protein product for functional analysis, as described infia. Once the nucleotide sequence is determined, an open reading frame encoding the CH gene protein product can be determined by any method well known in the art for determining open reading frames, for example, using publicly available computer programs for nucleotide sequence analysis. Once an open reading frame is defined, it is routine to determine the amino acid sequence of the protein encoded by the open reading frame. In this way, the amino acid sequences of CH-1, CH-2, CH-3, CH-4, CH-5, CH-6, CH-7, CH-8 and CH-9 can be determined from the nucleotide sequences of the corresponding genes. Thus, the nucleotide sequences of the entire CH genes as well as the amino acid sequences of CH proteins and analogs may be identified.

Any eukaryotic cell potentially can serve as the nucleic acid source for the molecular cloning of the CH gene. The nucleic acids can be isolated from vertebrate, mammalian, human, porcine, bovine, feline, avian, equine, canine, as well as additional primate sources, insects, plants, etc. The DNA may be obtained by standard procedures known in the art from cloned DNA (e.g., a DNA "library"), by chemical synthesis, by cDNA cloning, or by the cloning of genomic DNA, or fragments thereof, purified from the desired cell (see, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II). Clones derived from genomic DNA may contain regulatory and intronic DNA regions in addition to coding regions; clones derived from cDNA will contain only exonic sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNase in the presence of manganese to fragment the DNA, or the DNA can be physically sheared, for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, a portion of the CH (of any species) gene (e.g., a PCR amplification product obtained as described above or an oligonucleotide having a sequence of a portion of the known nucleotide sequence) or its specific RNA, or a fragment thereof be purified and labeled, and the generated DNA fragments may be screened by nucleic acid hybridization to the labeled probe (Benton and Davis, *Science* 196:180 (1977); Grunstein and Hogness, *Proc. Natl. Acad. Sci. U.S.A.* 72:3961 (1975)). Those DNA fragments with substantial homology to the probe will hybridize. It is also possible to identify the appropriate fragment by restriction enzyme digestion(s) and comparison of fragment sizes with those expected according to a known restriction map if such is available or by DNA sequence analysis and comparison to the known nucleotide sequence of CH. Further selection can be carried out on the basis of the properties of the gene. Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties or ability to activate T cell, as known for the CH. If an anti-CH antibody is available, the protein may be identified by binding of labeled antibody to the putatively CH synthesizing clones, in an ELISA (enzyme-linked immunosorbent assay)-type procedure.

Alternatives to isolating the CH genomic DNA include, but are not limited to, chemically synthesizing the gene sequence itself from a known sequence or making cDNA to the mRNA that encodes the CH protein. For example, RNA for cDNA cloning of the CH gene can be isolated from cells expressing the protein. Other methods are possible and within the scope of the invention.

The identified and isolated nucleic acids can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as pBR322 or pUC plasmid derivatives or the Bluescript vector (Stratagene, La Jolla, Calif.). The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and CH gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionation, can be done before insertion into the cloning vector.

In specific embodiments, transformation of host cells with recombinant DNA molecules that incorporate the isolated CH gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The CH sequences provided by the instant invention include those nucleotide sequences encoding substantially the same amino acid sequences as found in native CH proteins, and those encoded amino acid sequences with functionally equivalent amino acids, as well as those encoding other CH derivatives or analogs, as described in Section 5.1 supra for CH derivatives and analogs.

(2) Antibodies to CH Proteins

According to the invention, the CH protein and fragments, homologs and derivatives thereof may be used as immunogens to generate antibodies which immunospecifically bind such immunogens. Such antibodies include but are not limited to polyclonal, monoclonal, chimeric, single chain, Fab fragments, and an Fab expression library. In a specific embodiment, antibodies to human CH are produced. In another embodiment, complexes formed from fragments of CH, which fragments contain the protein domain that interacts with and activates T cell, are used as immunogens for antibody production.

Various procedures known in the art may be used for the production of polyclonal antibodies to CH protein, derivatives, fragments or analogs.

For production of the antibody, various host animals can be immunized by injection with the native CH protein or a synthetic version, or a derivative of the foregoing, such as a cross-linked CH, such host animals include but are not limited to rabbits, mice, rats, etc. Various adjuvants can be used to increase the immunological response, depending on the host species, and include but are not limited to Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as bacille Calmette-Guerin (BCG) and Corynebacterium parvum.

For preparation of monoclonal antibodies directed towards a CH or derivatives, fragments or analogs thereof, any technique that provides for the production of antibody molecules by continuous cell lines in culture may be used. Such techniques include but are not restricted to the hybridoma technique originally developed by Kohler and Milstein (*Nature* 256:495–497 (1975)), the trioma technique, the human B-cell hybridoma technique (Kozbor et al, *Immunology Today* 4:72 (1983)), and the EBV hybridoma technique to produce human monoclonal antibodies (Cole et al., in *Monoclonal Antibodies and Cancer Therapy*, Alan R. Liss, Inc., pp. 77–96 (1985)). In an additional embodiment of the invention, monoclonal antibodies can be produced in germ-free animals utilizing recent technology (PCT/US90/02545). According to the invention, human antibodies may be used and can be obtained by using human hybridomas (Cote et al., *Proc. Natl. Acad. Sci. USA* 80:2026–2030 (1983)). Or by transforming human B cells with EBV virus in vitro (Cole et al., in *Monoclonal Antibodies and Cancer Therapy*, Alan R. Liss, Inc., pp. 77–96 (1985)). In fact, according to the invention, techniques developed for the production of Achimeric antibodies (Morrison et al., *Proc. Natl. Acad. Sci. USA* 81:6851–6855 (1984); Neuberger et al., *Nature* 312:604–608 (1984); Takeda et al., *Nature* 314:452–454 (1985)) by splicing the genes from a mouse antibody molecule specific for the CH protein together with genes from a human antibody molecule of appropriate biological activity can be used; such antibodies are within the scope of this invention.

According to the invention, techniques described for the production of single chain antibodies (U.S. Pat. No. 4,946,778) can be adapted to produce CH-specific single chain antibodies. An additional embodiment of the invention utilizes the techniques described for the construction of Fab expression libraries (Huse et al., *Science* 246:1275–1281 (1989)) to allow rapid and easy identification of monoclonal Fab fragments with the desired specificity for CH or CH derivatives, or analogs thereof. Non-human antibodies can be "humanized" by known methods (see, e.g., U.S. Pat. No. 5,225,539).

Antibody fragments that contain the idiotypes of CH can be generated by techniques known in the art. For example, such fragments include but are not limited to: the $F(ab)_2$ fragment which can be produced by pepsin digestion of the antibody molecule; the Fab fragments that can be generated by reducing the disulfide bridges of the $F(ab)_2$ fragment, the Fab fragments that can be generated by treating the antibody molecular with papain and a reducing agent, and Fv fragments.

In the production of antibodies, screening for the desired antibody can be accomplished by techniques known in the art, e.g., ELISA (enzyme-linked immunosorbent assay). To select antibodies specific to a particular domain of the CH one may assay generated hybridomas for a product that binds to the fragment of the CH that contains such a domain Antibodies to specific domains of CH are also provided.

The foregoing antibodies can be used in methods known in the art relating to the localization and/or quantitation of CH proteins of the invention, e.g., for imaging these proteins, measuring levels thereof in appropriate physiological samples, in diagnostic methods, etc.

In another embodiment of the invention (see infra), anti-novel-CHAG antibodies, or fragments thereof, containing the binding domain are Therapeutics.

(3) Methods of Treatment

The present invention provides methods of treating and preventing cardiac hypertrophy diseases and disorders by administration of a therapeutic compound (termed herein "Therapeutic") of the invention. In one aspect of the invention, such "Therapeutics" include CHAG proteins and analogs, derivatives and fragments thereof (e.g., as described hereinabove) and nucleic acids encoding CHAG proteins, analogs, derivatives, or fragments (e.g., as described hereinabove), anti-CHAG antibodies, CHAG antisense nucleic acids, and modulators (i.e., agonists, antagonists and inhibitors) of CHAG.

The subject to which the Therapeutic is administered is preferably an animal, including but not limited to animals such as cows, pigs, horses, chickens, cats, dogs, etc., and is preferably a mammal. In a preferred embodiment, the subject is a human.

Generally, administration of products of a species origin or species reactivity (in the case of antibodies) that is the same species as that of the subject is preferred. Thus, in a preferred embodiment, a human CHAG protein, derivative, or analog, or nucleic acid, is therapeutically or prophylactically administered to a human patient.

The CHAG protein, derivative, or analog, or nucleic acid, or modulator of CHAG protein or nucleic acid, of the invention can be assayed by any of the methods described infra to determine whether increasing or decreasing activities of CHAG proteins or nucleic acids will treat or prevent cardiac hypertrophy. In the event it is determined that decreasing activities of a CHAG protein or nucleic acid will treat or prevent cardiac hypertrophy, then molecules that inhibit activities of CHAG proteins or nucleic acids, such as anti-CHAG antibodies, CHAG anti-sense nucleic acids, CHAG antagonists or inhibitors, are envisioned for use to treat or prevent cardiac hypertrophy, preferably pressure overload cardiac hypertrophy.

Accordingly, in a specific embodiment of the invention, CHAG antagonists and inhibitors, including but not limited to anti-CHAG antibodies (e.g. as described below) and CHAG anti-sense nucleic acids (e.g. as described below) and CHAG derivatives (e.g., that are competitive inhibitors of CHAG) are administered to treat or prevent cardiac hypertrophy, preferably pressure overload cardiac hypertrophy.

Alternatively, in the event it is determined that increasing the activity of a CHAG protein or nucleic acid will treat or prevent cardiac hypertrophy, CHAG proteins or nucleic acids and molecules that enhance CHAG activity are also envisioned for use to treat or prevent cardiac hypertrophy, preferably pressure overload cardiac hypertrophy.

Accordingly, in a specific embodiment of the invention, CHAG protein, nucleic acids or molecules that enhance CHAG activity are administered to treat or prevent cardiac hypertrophy, preferably pressure overload cardiac hypertrophy.

(4) Cardiac Hypertrophic Disease

In a preferred embodiment, Therapeutics of the invention are administered therapeutically, and preferably, prophylactically, to patients suffering from or in danger of suffering from cardiac hypertrophy disease, preferably pressure overload cardiac hypertrophy, have previously suffered a systematic hypertension or aortic stenosis event, or exhibit one or more "risk factors" for cardiac hypertrophy (i.e., a characteristic, behavior or disorder correlated with increased incidence of cardiac hypertrophy) or one or more conditions associated with cardiac hypertrophy. See Hutter, Jr., "Congestive Heart Failure", in Scientific American: Medicine, Volume 1(1:II), eds. Dale and Federman (Scientific American, Inc. 1994) and "Hypertrophic Cardiomyopathy", in The Merck Manual of Diagnosis and Therapy, Chapter 27, p519–522, eds. Berkow et al.,(Merck Sharp & Dohme Research Laboratories 1987).

Major indications of predisposition for cardiac hypertrophy predisposition are chest pains, syncope, palpitations, effort dyspnea or symptoms of aortic stenosis or coronary artery disease, or any combination the foregoing indications. Chest pain is usually typical angina related to exertion. Syncope is usually exertional, due to a combination of arrhythmia, outflow tract obstruction, and diastolic filling of the ventricle. Dyspnea on exertion is a result of poor diastolic compliance of the left ventricle that leads to rapid rise in LVEDP as flow increases. Palpitations are produced by ventricle or atrial arrhythmias.

Patients suffering from heart failure may also be predisposed to cardiac hypertrophy. By way of example but not by way of limitation, coronary artery disease, cardiomyopathy, myocarditis, aortic stenosis, hypertension, coarctation of the aorta, aortic regurgitation, mitral regurgitation, left-to-right shunts, restrictive cardiomyopathy, ischeric heart disease, pericardial tamponade, constrictive pericarditis, or restrictive cardiomyopathy can increase the likelihood that a patient will suffer a cardiac hypertrophy.

Therapeutics of the invention may also be administered with drugs which treat or ameliorate the effect of certain risk factors for cardiac hypertrophy. In a preferred embodiment, a Therapeutic of the invention is administered with one or more anti-cardiac-hypertrophy drug such as, but not limited to, β-Adrenoceptor blockers and $Ca^{2+}$-channel blockers, or carried out in conjunction with anti-arrhythmic therapy, antibiotic prophylaxis, or surgical treatment in the form of septal myotomy, myormectomy, or mitral valve replacement.

It is within the skill of those in the art to monitor and adjust the treatment or prophylactic regimen for treating or preventing cardiac hypertrophy disease while treating or preventing other potentially associated diseases or disorders, such as systematic hypertension.

(5) Gene Therapy

In a specific embodiment, nucleic acids comprising a sequence encoding a CHAG protein or functional derivative thereof, are administered to promote CHAG protein function, by way of gene therapy. Gene therapy refers to therapy performed by the administration of a nucleic acid to a subject. In this embodiment of the invention, the nucleic acid produces its encoded protein that mediates a therapeutic effect by promoting CHAG protein function.

Any of the methods for gene therapy available in the art can be used according to the present invention. Exemplary methods are described below. For general reviews of the methods of gene therapy, see Goldspiel et al., *Clinical Pharmacy* 12:488–505 (1993); Wu and Wu, *Biotherapy* 3:87–95 (1991); Tolstoshev, *Ann. Rev. Pharmacol. Toxicol.* 32:573–596 (1993); Mulligan, *Science* 260:926–932 (1993); and Morgan and Anderson, *Ann. Rev. Biochem.* 62:191–217 (1993); *TIBTECH* 11(5):155–215 (1993). Methods commonly known in the art of recombinant DNA technology are described in Ausubel et al., (eds.), *Current Protocols in Molecular Biology*, John Wiley & Sons, NY (1993); and Kriegler, *Gene Transfer and Expression, A Laboratory Manual*, Stockton Press, NY (1990).

In a preferred aspect of the present invention, the Therapeutic comprises a CHAG nucleic acid that is part of an expression vector that expresses a CHAG protein or fragment or chimeric protein thereof in a suitable host. In particular, such a nucleic acid has a promoter operably linked to the CHAG coding region, said promoter being inducible or constitutive, and, optionally, tissue-specific. In another particular embodiment, a nucleic acid molecule is used in which the CHAG coding sequences and any other desired sequences are flanked by regions that promote homologous recombination at a desired site in the genome, thus providing for intra-chromosomal expression of the CHAG nucleic acid (Koller and Smithies, *Proc. Natl. Acad. Sci. USA* 86:8932–8935 (1989); Zijlstra et al., *Nature* 342:435–438 (1989)).

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, DuPont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, *J. Biol. Chem.* 262:4429–4432 (1987)) (which can be used to target cell types specifically expressing the receptors), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.,); WO 92/22635 dated Dec. 23, 1992 (Wilson et al.,); WO92/20316 dated Nov. 26, 1992 (Findeis et al.,); WO93/14188 dated Jul. 22, 1993 (Clarke et al.,), WO 93/20221 dated Oct. 14, 1993 (Young)). Alternatively, the nucleic acid can be introduced intracellularly and incorporated within host cell DNA for expression, by homologous recombination (Koller and Smithies, *Proc. Natl. Acad. Sci. USA* 86:8932–8935 (1989); Zijlstra et al., *Nature* 342:435–438 (1989)).

In a specific embodiment, a viral vector that contains the CHAG nucleic acid is used. For example, a retroviral vector can be used (see Miller et al., *Meth. Enzymol.* 217:581–599 (1993)). These retroviral vectors have been modified to delete retroviral sequences that are not necessary for packaging of the viral genome and integration into host cell DNA. The CHAG nucleic acid to be used in gene therapy is cloned into the vector, which facilitates delivery of the gene into a patient. More detail about retroviral vectors can be found in Boesen et al., *Biotherapy* 6:291–302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., *J. Clin. Invest.* 93:644–651 (1994); Kiem et al., *Blood* 83:1467–1473 (1994); Salmons and Gunzberg, *Human Gene Therapy* 4:129–141 (1993); and Grossman and Wilson, *Curr. Opin. in Genetics and Devel.* 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics and Development* 3:499–503 (1993) present a review of adenovirus-based gene therapy. Bout et al, *Human Gene Therapy* 5:3–10 (1994) demonstrated the use of adenovirus vectors to transfer genes to the respiratory epithelia of rhesus 5 monkeys. Other instances of the use of Adenoviruses in gene therapy can be found in Rosenfeld et al., *Science* 252:431–434 (1991); Rosenfeld et al., *Cell* 68:143–155 (1992); and Mastrangeli et al., *J. Clin. Invest.* 91:225–234 (1993).

Adeno-associated virus (AAV) has also been proposed for use in gene therapy (Walsh et al., *Proc. Soc. Exp. Biol. Med.* 204:289–300 (1993).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, *Meth. Enzymol.* 217:599–618 (1993); Cohen et al., *Meth. Enzymol.* 217:618–644 (1993); Cline, *Pharmac. Ther.* 29:69–92 (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells may be applied as a skin graft onto the patient. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T-lymphocytes, B-lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient. In another embodiment in which recombinant cells are used in gene therapy, a CHAG nucleic acid is introduced into the cells such that it is expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention. Such stem cells include but are not limited to hematopoietic stem cells (HSC), stem cells of epithelial tissues such as the skin and the lining of the gut, embryonic heart muscle cells, liver stem cells (PCT Publication WO 94/08598, dated Apr. 28, 1994), and neural stem cells (Stemple and Anderson, *Cell* 71:973–985 (1992)).

Epithelial stem cells (ESCs) or keratinocytes can be obtained from tissues such as the skin and the lining of the gut by known procedures (Rheinwald, *Meth. Cell Bio.* 21A:229 (1980)). In stratified epithelial tissue such as the skin, renewal occurs by mitosis of stem cells within the germinal layer, the layer closest to the basal lamina. Stem cells within the lining of the gut provide for a rapid renewal rate of this tissue. ESCs or keratinocytes obtained from the skin or lining of the gut of a patient or donor can be grown in tissue culture (Rheinwald, *Meth. Cell Bio.* 21A:229 (1980); Pittelkow and Scott, *Mayo Clinic Proc.* 61:771 (1986)). If the ESCs are provided by a donor, a method for suppression of host versus graft reactivity (e.g., irradiation, drug or antibody administration to promote moderate immunosuppression) can also be used.

With respect to hematopoietic stem cells (HSC), any technique which provides for the isolation, propagation, and maintenance in vitro of HSC can be used in this embodiment of the invention. Techniques by which this may be accomplished include, but are not limited to: (a) the isolation and establishment of HSC cultures from bone marrow cells isolated from the future host, or a donor or (b) the use of previously established long-term HSC cultures, which may be allogeneic or xenogeneic. Non-autologous HSC are used preferably in conjunction with a method of suppressing transplantation immune reactions of the future host/patient. In a particular embodiment of the present invention, human bone marrow cells can be obtained from the posterior iliac crest by needle aspiration (see, e.g., Kodo et al., *J. Clin. Invest.* 73:1377–1384 (1984)). In a preferred embodiment of the present invention, the HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., *J. Cell Physiol.* 91:335 (1977) or Witlock-Witte culture techniques (Witlock and Witte, *Proc. Natl. Acad. Sci. USA* 79:3608–3612 (1982)).

In a specific embodiment, the nucleic acid to be introduced for purposes of gene therapy comprises an inducible promoter operably-linked to the coding region, such that nucleic acid expression is controllable by the presence or absence of the appropriate inducer of transcription.

(6) Therapeutic Utilization of CHAG Antisense Nucleic Acids

In a specific embodiment, as described hereinabove, CHAG function is reduced or inhibited by CHAG antisense nucleic acids, to treat or prevent cardiac hypertrophy, preferably pressure overload cardiac hypertrophy. The present invention provides the therapeutic or prophylactic use of nucleic acids of at least six nucleotides that are antisense to a gene or cDNA encoding CHAG or a portion thereof. An CHAG "antisense" nucleic acid as used herein refers to a nucleic acid capable of hybridizing to a portion of an CHAG RNA (preferably mRNA) by virtue of some sequence complementarily. The antisense nucleic acid may be complementary to a coding and/or noncoding region of an CHAG mRNA. Such antisense nucleic acids have utility as Therapeutics that reduce or inhibit CHAG function, and can be used in the treatment or prevention of disorders as described supra.

The CHAG antisense nucleic acids are of at least six nucleotides and are preferably oligonucleotides (ranging from 6 to about 150 nucleotides, or more preferably 6 to 50 nucleotides). In specific aspects, the oligonucleotide is at least 10 nucleotides, at least 15 nucleotides, at least 100 nucleotides, or at least 125 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., *Proc. Natl. Acad. Sci. U.S.A.* 86:6553–6556 (1989); Lemaitre et al., *Proc. Natl. Acad. Sci. U.S.A.* 84:648–652 (1987); PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., *BioTechniques* 6:958–976 (1988)) or intercalating agents (see, e.g., Zon, *Pharm. Res.* 5:539–549 (1988)).

The CHAG antisense nucleic acid is preferably an oligonucleotide, more preferably of single-stranded DNA. In a preferred aspect, the oligonucleotide comprises a sequence antisense to a portion of human CHAG. The oligonucleotide may be modified at any position on its structure with substituents generally known in the art.

The CHAG antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, β-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, β-D-mannosylqueosine, 5N-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

In another embodiment, the oligonucleotide comprises at least one modified sugar moiety selected from the group including but not limited to arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an α-anomeric oligonucleotide. An α-anomeric oligonucleotide forms specific double-stranded hybrids with complementary RNA in which, contrary to the usual β-units, the strands run parallel to each other (Gautier et al., *Nucl. Acids Res.* 15:6625–6641 (1987)).

The oligonucleotide may be conjugated to another molecule, e.g., a peptide, hybridization triggered cross-linking agent, transport agent, hybridization-triggered cleavage agent, etc.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al., (*Nucl. Acids Res.* 16:3209 (1988)), methylphosphonate oligonucleotides can be prepared by use of controlled pore glass polymer supports (Sarin et al., *Proc. Natl. Acad. Sci. U.S.A.* 85:7448–7451 (1988)), etc.

In a specific embodiment, the CHAG antisense oligonucleotide comprises catalytic RNA, or a ribozyme (see, e.g., PCT International Publication WO 90/11364, published Oct. 4, 1990; Sarver et al., *Science* 247:1222–1225 (1990)). In another embodiment, the oligonucleotide is a 2N-O-methylribonucleotide (Inoue et al., *Nucl. Acids Res.* 15:6131–6148 (1987)), or a chimeric RNA-DNA analogue (Inoue et al., *FEBS Lett.* 215:327–330 (1987)).

In an alternative embodiment, the CHAG antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the CHAG antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the CHAG antisense RNA can be by any promoter known in the art to act in mammalian, preferably human, cells. Such promoters can be inducible or constitutive. Such promoters include but are not limited to: the SV40 early promoter region (Bernoist and Chambon, *Nature* 290:304–310 (1981), the promoter contained in the 3N long terminal repeat of Rous sarcoma virus (Yamamoto et al., *Cell* 22:787–797 (1980), the herpes thymidine kinase promoter (Wagner et al., *Proc. Natl. Acad. Sci. U.S.A.* 78:1441–1445 (1981), the regulatory sequences of the metallothionein gene (Brinster et al., *Nature* 296:39–42 (1982), etc.

The antisense nucleic acids of the invention comprise a sequence complementary to at least a portion of an RNA transcript of an CHAG gene, preferably a human CHAG gene. However, absolute complementarily, although preferred, is not required. A sequence "complementary to at least a portion of an RNA," as referred to herein, means a sequence having sufficient complementarily to be able to hybridize with the RNA, forming a stable duplex; in the case of double-stranded CHAG antisense nucleic acids, a single strand of the duplex DNA may thus be tested, or triplex formation may be assayed. The ability to hybridize will depend on both the degree of complementarily and the length of the antisense nucleic acid. Generally, the longer the hybridizing nucleic acid, the more base mismatches with a an CHAG RNA it may contain and still form a stable duplex (or triplex, as the case may be). One skilled in the art can ascertain a tolerable degree of mismatch by use of standard procedures to determine the melting point of the hybridized complex.

The invention further provides pharmaceutical compositions comprising an effective amount of the CHAG antisense nucleic acids of the invention in a pharmaceutically acceptable carrier, as described infra. In a specific embodiment, pharmaceutical compositions comprising CHAG antisense nucleic acids are administered via liposomes, microparticles, or microcapsules. In various embodiments of the invention, it may be useful to use such compositions to achieve sustained release of the CHAG antisense nucleic acids.

The amount of CHAG antisense nucleic acid which will be effective in the treatrment or prevention of ischemic disease will depend on the nature of the disease, and can be determined by standard clinical techniques. Where possible, it is desirable to determine the antisense cytotoxicity in cells in vitro, and then in useful animal model systems prior to testing and use in humans. Additional methods that can be adapted for use to deliver a CHAG antisense nucleic acid are described infra.

(7) Diagnosis and Screening

CHAG proteins, analogs, derivatives, and subsequences thereof, CHAG nucleic acids (and sequences complementary thereto), and anti-CHAG antibodies, have uses in diagnostics. Such molecules can be used in assays, such as immunoassays, to detect, prognose, diagnose, or monitor various conditions, diseases, and disorders affecting CHAG expression, or monitor the treatment thereof. In particular, such an immunoassay is carried out by a method comprising contacting a sample derived from a patient with an anti-CHAG antibody under conditions such that immunospecific binding can occur, and detecting or measuring the amount of any immunospecific binding by the antibody. In a specific aspect, such binding of antibody, in tissue sections, can be used to detect aberrant CHAG localization or aberrant (e.g., low or absent) levels of CHAG protein. In a specific embodiment, antibody to CHAG protein can be used to assay in a patient tissue or serum sample for the presence of CHAG protein where an aberrant level of CHAG protein is an indication of a diseased condition. By "aberrant levels," is meant increased or decreased levels relative to that present, or a standard level representing that present, in an analogous sample from a portion of the body or from a subject not having the disorder.

The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

CHAG genes and related nucleic acid sequences and subsequences, including complementary sequences, can also be used in hybridization assays. CHAG nucleic acid sequences, or subsequences thereof comprising about at least 8 nucleotides, can be used as hybridization probes. Hybridization assays can be used to detect, prognose, diagnose, or monitor conditions, disorders, or disease states associated with aberrant changes in CHAG expression and/or activity as described supra. In particular, such a hybridization assay is carried out by a method comprising contacting a sample containing nucleic acid with a nucleic acid probe capable of hybridizing to CHA G DNA or RNA, under conditions such that hybridization can occur, and detecting or measuring any resulting hybridization.

In specific embodiments, diseases and disorders involving cardiac hypertrophy can be diagnosed, or their suspected presence can be screened for, or a predisposition to develop such disorders can be detected, by detecting decreased levels of CHAG genes or proteins that are down-regulated in hypertrophic cardiac tissue, in comparison to normal cardiac tissue (erg. CH-1, Desmin, Protein Kinase C-Binding Protein β15, genes encoding 5.8S, 18S and 28S rRNAs) or CHAG functional activity, or by detecting mutations in CHAG RNA, DNA or protein (erg, translocations in CHAG nucleic acids, truncations in the CHAG gene or protein, changes in nucleotide or amino acid sequence relative to wild-type CHAG) that cause decreased expression or activity of CHAG. Such diseases and disorders include but are not limited to those described in Section 5.4.1. By way of example, levels of CHAG protein can be detected by immunoassay, levels of CHAG RNA can be detected by QEA or hybridization assays (erg., Northern blots, dot blots), CHAG protein binding to their binding partners can be done by binding assays commonly known in the art, translocations and point mutations in CHAG nucleic acids can be detected by Southern blotting, RFLP analysis, PCR using primers that preferably generate a fragment spanning at least most of the CHAG gene, sequencing of the CHAG genomic DNA or cDNA obtained from the patient, etc.

In another specific embodiment, diseases and disorders involving cardiac hypertrophy, are diagnosed, or their suspected presence can be screened for, or a predisposition to develop such disorders can be detected, by detecting increased levels of CHAG proteins or RNA that are upregulated in hypertrophic cardiac tissue as compared to control tissue (e.g., CH-2, CH-3, CH-4, CH-5, CH-6, CH-7, CH-8, CH-9, α-Enolase, Antizyme Inhibitor, Biglycan, Cytochrome Oxidase I, Cytochrome Oxidase II, Cyclin G, D-binding protein, Fibrillin, Laminin α-1, p85, and Preproenkephalin protein) or CHAG functional activity, or by detecting mutations in CHAG RNA, DNA or protein (e.g., translocations in CHAG nucleic acids, truncations in the gene or protein, changes in nucleotide or amino acid sequence relative to wild-type CHAG) that cause increased expression or activity of CHAG. Such diseases and disorders include but are not limited to those described in infta. By way of example, levels of CHAG protein, levels of CHAG RNA, CHAG DNA, CHAG binding activity, and the presence of translocations or point mutations can be determined as described above.

Kits for diagnostic use are also provided, that comprise in one or more containers an anti-CHAG antibody, and, optionally, a labeled binding partner to the antibody. Alternatively, the anti-CHAG antibody can be labeled (with a detectable marker, e.g., a chemiluminescent, enzymatic, fluorescent, or radioactive moiety). A kit is also provided that comprises in one or more containers a nucleic acid probe capable of hybridizing to CHAG RNA. In a specific embodiment, a kit can comprise in one or more containers a pair of primers (e.g., each in the size range of 6–30 nucleotides) that are capable of priming amplification [e.g., by polymerase chain reaction (see e.g., Innis et al., 1990, PCR Protocols, Academic Press, Inc., San Diego, Calif.), ligase chain reaction (see EP 320,308) use of Qβ replicase, cyclic probe reaction, or other methods known in the art] under appropriate reaction conditions of at least a portion of a CHAG nucleic acid. A kit can optionally further comprise in a container a predetermined amount of a purified CHAG protein or nucleic acid, e.g. for use as a standard or control.

(8) Screening for CHAG Modulators

CHAG nucleic acids, proteins, and derivatives also have uses in screening assays to detect molecules that specifically bind to CHAG nucleic acids, proteins, or derivatives and thus have potential use as agonists or antagonists of CHAG, in particular, molecules that thus affect cardiac hypertrophy. In a preferred embodiment, such assays are performed to screen for molecules with potential utility as anti-cardiac-hypertrophy agents for drug development. The invention thus provides assays to detect molecules that specifically bind to CHAG nucleic acids, proteins, or derivatives. For example, recombinant cells expressing CHAG nucleic acids can be used to recombinantly produce CHAG proteins in these assays, to screen for molecules that bind to a CHAG protein. Molecules (e.g., putative binding partners of CHAG) are contacted with the CHAG protein (or fragment thereof) under conditions conducive to binding, and then molecules that specifically bind to the CHAG protein are identified. Similar methods can be used to screen for molecules that bind to CHAG derivatives or nucleic acids. Methods that can be used to carry out the foregoing are commonly known in the art.

By way of example, diversity libraries, such as random or combinatorial peptide or non-peptide libraries can be screened for molecules that specifically bind to CHAG. Many libraries are known in the art that can be used, e.g., chemically synthesized libraries, recombinant (e.g., phage display libraries), and in vitro translation-based libraries.

Examples of chemically synthesized libraries are described in Fodor et al., *Science* 251:767–773 (1991); Houghten et al., *Nature* 354:84–86 (1991); Lam et al., *Nature* 354:82–84 (1991); Medynski, *Bio/Technology* 12:709–710 (1994); Gallop et al., *J. Medicinal Chemistry* 37(9):1233–1251 (1994); Ohlmeyer et al., *Proc. Natl. Acad. Sci. USA* 90:10922–10926 (1993); Erb et al., *Proc. Natl. Acad. Sci. USA* 91:11422–11426 (1994); Houghten et al., *Biotechniques* 13:412 (1992); Jayawickreme et al., *Proc. Natl. Acad. Sci. USA* 91:1614–1618 (1994); Salmon et al., *Proc. Natl. Acad. Sci. USA* 90:11708–11712 (1993); PCT Publication No. WO 93/20242; and Brenner and Lerner, *Proc. Natl. Acad. Sci. USA* 89:5381–5383 (1992).

Examples of phage display libraries are described in Scott and Smith, *Science* 249:386–390 (1990); Devlin et al., *Science* 249:404–406 (1990); Christian, R. B., et al., *J. Mol. Biol.* 227:711–718 (1992); Lenstra, *J. Immunol. Meth.* 152:149–157 (1992); Kay et al., *Gene* 128:59–65 (1993); and PCT Publication No. WO 94/18318 dated Aug. 18, 1994.

In vitro translation-based libraries include but are not limited to those described in PCT Publication No. WO 91/05058 dated Apr. 18, 1991; and Mattheakis et al., *Proc. Natl. Acad. Sci. USA* 91:9022–9026 (1994).

By way of examples of non-peptide libraries, a benzodiazepine library (see e.g., Bunin et al., *Proc. Natl. Acad. Sci. USA* 91:4708–4712 (1994)) can be adapted for use. Peptide libraries (Simon et al., *Proc. Natl. Acad. Sci. USA* 89:9367–9371 (1992)) can also be used. Another example of a library that can be used, in which the amide functionalities in peptides have been permethylated to generate a chemically transformed combinatorial library, is described by Ostresh et al., *Proc. Natl. Acad. Sci. USA* 91:11138–11142 (1994).

Screening the libraries can be accomplished by any of a variety of commonly known methods. See, e.g., the following references, which disclose screening of peptide libraries: Parmley and Smith, *Adv. Exp. Med Biol.* 251:215–218 (1989); Scott and Smith, *Science* 249:386–390 (1990); Fowlkes et al., *BioTechniques* 13:422–427 (1992); Oldenburg et al., *Proc. Natl. Acad. Sci. USA* 89:5393–5397 (1992); Yu et al., *Cell* 76:933–945 (1994); Staudt et al., *Science*

241:577–580 (1988); Bock et al., *Nature* 355:564–566 (1992); Tuerk et al, *Proc. Natl. Acad. Sci. USA* 89:6988–6992 (1992); Ellington et al., *Nature* 355:850–852 (1992); U.S. Pat. No. 5,096,815, U.S. Pat. No. 5,223,409, and U.S. Pat. No. 5,198,346, all to Ladner et al.,; Rebar and Pabo, *Science* 263:671–673 (1993); and PCT Publication No. WO 94/18318.

In a specific embodiment, screening can be carried out by contacting the library members with a CHAG protein (or nucleic acid or derivative) immobilized on a solid phase and harvesting those library members that bind to the protein (or nucleic acid or derivative). Examples of such screening methods, termed "panning" techniques are described by way of example in Parmley and Smith, *Gene* 73:305–318 (1988); Fowlkes et al., *BioTechniques* 13:422–427 (1992); PCT Publication No. WO 94/18318; and in references cited hereinabove.

In another embodiment, the two-hybrid system for selecting interacting proteins in yeast (Fields and Song, *Nature* 340:245–246 (1989); Chien et al., *Proc. Natl. Acad. Sci. USA* 88:9578–9582 (1991)) can be used to identify molecules that specifically bind to a CHAG protein or derivative.

(9) Assays for CHAG and Derivatives and Analogs Thereof

The functional activity of CHAG proteins, and derivatives, fragments and analogs thereof can be assayed by various methods. Potential modulators (e.g., inhibitors, agonists and antagonists) of CHAG activity, e.g., anti-CHAG antibodies and CHAG antisense nucleic acids can be assayed for the ability to modulate expression and/or activity of CHAG.

For example, in one embodiment, where one is assaying for the ability to bind or compete with wild-type CHAG for binding to an anti-CHAG antibodies, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

The expression of the CHAG genes (both endogenous genes and those expressed from cloned DNA containing these genes) can be detected using techniques known in the art, including but not limited to Southern hybridization (Southern, *J. Mol. Biol.* 98: 503–517 (1975), northern hybridization (e.g. Freeman et al., *Proc. Natl. Acad. Sci. USA* 80: 4094–4098 (1983), restriction endonuclease mapping (Sambrook et al., 1982, *Molecular Cloning, A Laboratory Manual*, Cold Spring Harbor Press, New York), and DNA sequence analysis. Polymerase chain reaction amplification (PCR; U.S. Pat. Nos. 4,683,202, 4,683,195, and 4,889,818; Gyllenstein et al., *Proc. Natl. Acad. Sci. USA* 85: 7652–7657 (1988); Ochman et al., *Genetics* 120: 621–623 (1988); Loh et al., *Science* 243: 217–220 (1989)) followed by Southern hybridization or RNase protection (*Current Protocols in Molecular Biology*, John Wiley and Sons, New York, 1997) with probes specific for CHAG genes in various cell types. Methods of amplification other than PCR commonly known in the art can be employed. In one embodiment, Southern hybridization can be used to detect genetic linkage of CHAG gene mutations to physiological or pathological states. Various cell types, at various stages of development, can be characterized for their expression of CHAG expression. The stringency of the hybridization conditions for northern or Southern blot analysis can be manipulated to ensure detection of nucleic acids with the desired degree of relatedness to the specific probes used. Modifications to these methods and other methods commonly known in the art can be used.

In one embodiment, a Therapeutic of the invention can be assayed for activity in treating or preventing cardiac hypertrophy by contacting cultured cells that exhibit an indicator of a cardiac hypertrophy disease in vitro with the Therapeutic; and comparing the level of said indicator in the cells contacted with the Therapeutic, with said level of said indicator in cells not so contacted, wherein an altered level of such indicators in said contacted cells indicates that the Therapeutic has activity in treating or preventing cardiac hypertrophy disease. In vitro models for cardiac hypertrophy include, but are not limited to: cultured myocytes isolated from neonate and adult hearts, isolated papillary muscles, skinned fibers, and beating or arrested isolated perfused hearts subjected to various pressure and volume-loading conditions (Cooper et al., *J. Mol. Cell. Cardiol.* 21(Suppl 5):11–301 (1989); Simpson et al., *J. Mol. Cell. Cardiol.* 21(Suppl 5):79–89 (1989); Morgan and Baker, *Circulation* 83:13–251991; Chien et al., *FASEB. J.* 5:3037–3046 (1991); Schneider and Parker, *Mol. Biol. Med.* 8:167–183 (1991)). Specific examples of such cardiac hypertrophy indicators include, but are not limited to: increased myocardial cell size (Simpson et al., *J. Clin. Invest.* 72:732–738 (1983)), an increase in the assemble of an individual contractile protein (MLC-2) into organized contractile units (Iwaki et al., *J. Biol. Chem.* 265:13809–13817 (1990)), accumulation of contractile proteins (Lee et al., *J. Biol. Chem.* 263::7352–7358 (1988)), increased protein content per cell (Lai et al., *Am. J. Physiol.* 271:H2197–H2208 (1996)), activation of the β-MHC gene and repression of the α-MHC gene (Lompréet al., *Int. Rev. Cytol.* 124:137–186 (1991)), transient up-regulation of α-skeletal isoactin gene (Izumo et al., *Proc. Natl. Acad. Sci. USA* 85:339–343 (1988)); permanent reactivation of α-smooth actin isoform (Black et al., *J. Clin. Invest.* 88:1581–1588 (1991)), increased expression of myosin light chains 1 and 2 (Cummins, *Biochem. J.* 205:195–204 (1982)), transient activation of β isoform of tropomyosin (Izumo et al., *Proc. Natl. Acad. Sci. USA* 85:339–343 (1988)), increased expression of fetal type isoenzymes (BB+MB) of creatine kinase and of the M-LDH isoform of lactate dehydrogenase (Ingwall et al., *N. Engl. J. Med.* 313:1050–1054 (1985)), accumulation of the fetal forms of cellular fibronectin in the wall of coronary arteries and in focal areas of the myocardium early after rat aortic stenosis (Samuel et al., *J. Clin. Invest.* 88: 1737–1746 (1991)), transient upregulation of c-fos, c-myc, c-jun, junB, and nur 77 (Komuro et al., *Circ. Res.* 62:1075–1079 (1988); Izumo et al., *Proc. Nat]. Acad. Sci. USA* 85:339–343 (1988); Rockman et al., *Proc. Nat]. Acad. Sci. USA* 88:8277–8281 (1991)), a transient and early expression of three heat-shock proteins (HSP70, HSP68, and HSP58) (Delcayre et al, *J. Clin. invest.* 82:460–468 (1988)), accumulation of mRNAs encoding transforming growth factor β1 (TGFβ1), insulin like growth factor-I, and early growth response factor 1 (Egr-1), a serum-inducible zinc finger protein (Schneider and Parker, *Mol. Biol. Med.* 8:167–183 (1991); Chien et al., *FASEB. J.* 5:3037–3046 (1991)), the ventricular expression of atrial natriuretic factor (ANF) (Mercadier and Michael, In Swynghedauw B, ed. Research in Cardiac Hypertrophy and Failure. Paris, INSERM/John Libbey Eurotext, pp 401–413 (1990)), and the decreased expression of the slow skeletal/cardiac form SERCA2a isoform of the $Ca^{2+}$ ATPase of the sarcoplasmic reticulum (Komuro et al., *J. Clin. Invest.* 83:1102–1108 (1989); Nagai et al., *Proc. Natl. Acad. Sci. USA* 86:2966–2970 (1989); De la Bastie et al., Circ. Res. 66:554–564 (1990); Mercadier et al., *J. Clin. Invest.* 85:305–309 (1990)).

In another embodiment, a Therapeutic of the invention can be assayed for activity in treating or preventing cardiac hypertrophy by administering the Therapeutic to a test animal that exhibits one or more symptoms of a cardiac hypertrophy disease, or that is predisposed to develop symptoms of a cardiac hypertrophy disease; and measuring the change in said symptoms of the cardiac hypertrophy disease after administration of said Therapeutic, wherein a reduction in the severity of the symptoms of the cardiac hypertrophy or prevention of the symptoms of the cardiac hypertrophy disease indicates that the Therapeutic has activity in treating or preventing cardiac hypertrophy disease. Such a test animal can be any one of a number of animal models known in the art for cardiac hypertrophy disease. Cardiac hypertrophy can be induced by either mechanical triggers via stretch, load, cell deformation, and contraction, and by trophic triggers such as peptide derived growth factors (including, fibroblast growth factors, transforming growth factors, angiotensin II, and endothelin), thyroxine, adrenocorticoids, insulin, growth hormone, or adrenoreceptor activation (Boheler and Schwartz, *TCM* 2(5):176–182 (1992)). Animal models include but are not limited to: cardiac hypertrophy induced by chronic or acute administration of adrenergic agonists or antagonists, thyroxine, angiotensin II, converting enzyme inhibitors (Boheler and Schwartz, *TCM* 2(5): 176–182 (1992)), and endothelin-1 (Shubeita el al., *J. Biol. Chem.* 265(33):20555–20562 (1990)), and by surgical procedures that produce constriction of aorta, aortic incompetence, and aortocaval fistula (Mercadier et al., *Circ. Res.* 49:525–532 (1991)), and in the spontaneous hypertensive rat (SHR) (Boluyt et al., *Circ. Res.* 75:23–32 (1994)). Symptoms of the cardiac hypertrophy in the animal models include but are not limited to: an increase in the absolute heart weight and heart weight-to-body weight ratio, and absolute ventricular weight and ventricular-weight-to-body weight ratio (Lai, et al., *Am. J. Physiol.* 271:H2197–H2208 (1996)), and any of the cardiac hypertrophy indicators discussed in the preceding paragraph.

(10) Pharmaceutical Compositions

The invention provides methods of treatment and prophylaxis by administering to a subject of an effective amount of a Therapeutic of the invention. In a preferred aspect, the Therapeutic is substantially purified. The subject is preferably an animal, including but not limited to animals such as cows, pigs, horses, chickens, cats, dogs, etc., and is preferably a mammal, and most preferably human. In a specific embodiment, a non-human mammal is the subject.

Formulations and methods of administration that can be employed when the Therapeutic comprises a nucleic acid are described supra; additional appropriate formulations and routes of administration can be selected from among those described hereinbelow.

Various delivery systems are known and can be used to administer a Therapeutic of the invention, e.g., encapsulation in liposomes, microparticles, microcapsules, recombinant cells capable of expressing the Therapeutic, receptor-mediated endocytosis (see, e.g., Wu and Wu, *J. Biol. Chem.* 262:4429–4432 (1987)), construction of a Therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In another embodiment, the Therapeutic can be delivered in a vesicle, in particular a liposome (see Langer, *Science* 249:1527–1533 (1990); Treat et al., in Liposomes in the Therapy of Infectious Disease and Cancer, Lopez-Berestein and Fidler (eds.), Liss, N.Y., pp. 353–365 (1989); Lopez-Berestein, ibid., pp. 317–327; see generally ibid.)

In yet another embodiment, the Therapeutic can be delivered in a controlled release system. In one embodiment, a pump may be used (see Langer, supra; Sefton, CRC Crit Ref *Biomed. Eng.* 14:201 (1987); Buchwald et al., *Surgery* 88:507 (1980); Saudek et al., *N. Engl. J Med.* 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, *J. Macromol. Sci. Rev. Macromol. Chem.* 23:61 (1983); see also Levy et al., *Science* 228:190 (1985); During et al., *Am. Neurol.* 25:351 (1989); Howard et al., *J. Neurosurg.* 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (*Science* 249:1527–1533 (1990)).

In a specific embodiment where the Therapeutic is a nucleic acid encoding a protein Therapeutic, the nucleic acid can be administered in vivo to promote expression of its encoded protein by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, DuPont), or coating with lipids or cell-surface receptors or transfecting agents, or by administering it in linkage to a homeobox-like peptide which is known to enter the nucleus (see e.g., Joliot et al., *Proc. Natl. Acad. Sci. USA* 88:1864–1868 (1991)), etc. Alternatively, a nucleic acid Therapeutic can be introduced intracellularly and incorporated within host cell DNA for expression, by homologous recombination.

The present invention also provides pharmaceutical compositions. Such compositions comprise a therapeutically effective amount of a Therapeutic, and a pharmaceutically acceptable carrier. In a specific embodiment, the term "pharmaceutically acceptable" means approved by a regulatory agency of the Federal or a state government or listed in the U.S. Pharmacopoeia or other generally recognized pharmacopoeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 μg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

(11) Animal Models

The invention also provides animal models. In one embodiment, animal models for diseases and disorders involving cardiac hypertrophy are provided. Such an animal can be initially produced by promoting homologous recombination between a CH gene in its chromosome and an exogenous CH gene that has been rendered biologically inactive (preferably by insertion of a heterologous sequence, e.g., an antibiotic resistance gene). In a preferred aspect, this homologous recombination is carried out by transforming embryo-derived stem (ES) cells with a vector containing the insertionally-inactivated CH gene, such that homologous recombination occurs, followed by injecting the ES cells into a blastocyst, and implanting the blastocyst into a foster mother, followed by the birth of the chimeric animal ("knockout animal") in which a CH gene has been inactivated (see Capecchi, *Science* 244:1288–1292 (1989)). The chimeric animal can be bred to produce additional knockout animals. Such animals can be mice, hamsters, sheep, pigs, cattle, etc., and are preferably non-human mammals. In a specific embodiment, a knockout mouse is produced.

Such knockout animals are expected to develop or be predisposed to developing diseases or disorders involving cardiac hypertrophy and thus can have use as animal models of such diseases and disorders, e.g., to screen for or test molecules for the ability to treat or prevent such diseases or disorders.

In a separate embodiment, animal models for diseases and disorders involving cardiac hypertrophy are provided. Such an animal can be initially produced by promoting homologous recombination between a CH gene in its chromosome and an exogenous CH gene that would be over-expressed or mis-expressed (preferably by expression under a strong promoter). In a preferred aspect, this homologous recombination is carried out by transforming embryo-derived stem (ES) cells with a vector containing the over-expressed or mis-expressed CH gene, such that homologous recombination occurs, followed by injecting the ES cells into a blastocyst, and implanting the blastocyst into a foster mother, followed by the birth of the chimeric animal in which a CH gene has been over-expressed or mis-expressed (see Capecchi, *Science* 244:1288–1292 (1989)). The chimeric animal can be bred to produce additional knockout animals. Such animals can be mice, hamsters, sheep, pigs, cattle, etc., and are preferably non-human mammals. In a specific embodiment, a knockout mouse is produced.

Such animals are expected to develop or be predisposed to developing diseases or disorders involving cardiac hypertrophy and thus can have use as animal models of such diseases and disorders, e.g., to screen for or test molecules for the ability to inhibit function of CH genes and proteins and thus treat or prevent such diseases or disorders.

(12) Specific Examples

To obtain a more detailed understanding of the changes in gene expression occurring during pressure overload hypertrophy, QEA was used to identify expression differences in a rat surgical model of pressure overload (POL) induced cardiac hypertrophy. This in vivo model is attractive for expression analysis as there are limited changes in tissue cellularity by infiltration of non-resident cells. The tissue reaction to acute POL is primarily due to an intrinsic response of the myocardium including hypertrophy of the cardiomyocytes, in addition to hyperplasia of endothelial, smooth muscle, and mesenchymal cells (Weber and Brilla, *Circulation* 83:1849–1865 (1991); Cooper, IV, *Ann. Rev. Physiol.* 49:501–518 (1987)). While this process is initially adaptive, there is ultimately a deterioration of contractile function accompanied by interstitial and perivascular fibrosis and increased wall stiffness (Kimura et al., *Heart Circ. Physiol.* 25:H1006–H1011 (1989); Batra and Rakusan, *J. Cardiovasc. Pharmacol.* 17 (Suppl 2):S151–S153 (1991)). Abdominal aortic constriction leads to moderate hemodynamic overload (Boheler and Schwartz, *TCM* 2:176–182 (1992); Grossman et al., *J. Clin. Invest.* 56:56–64 (1975)), with the heart responding by concentric hypertrophy of the left ventricle, a process that leads to normalization of systolic wall stress (Morgan and Baker, *Circulation* 83:13–25 (1991)). Although increased load is thought to be the primary stimulus for this response, focal necrosis in the myocardium may also contribute to increased wall stress in this model.

(a) Materials and Methods

Total cellular RNA was extracted from 5 mg of heart tissue by first grinding the tissue into a fine powder on liquid nitrogen. The tissue powder was transferred to a tube containing 500 µl Triazol reagent (see Chomszynski et al., 1987. *Annal. Biochem.* 162 156–159 and Chomszynski et al., 1993, *Biotechniques* 15:532–532,536–537; reagent obtained from Life Technologies, Gaithersburg, Md.) and was dispersed in the Triazol using a Polytron homogenizer from Brinkman Instruments (Westbury, N.Y.). The cellular RNA fraction was extracted with 50 µl BCP (1-bromo-3-chloropropane) (Molecular Research. Cincinnati, Ohio). The extraction mixture was centrifuged for 15 minutes at 4° C. at 12,000×G, and the aqueous phase was removed to a fresh tube. The RNA was then precipitated with 0.5 volumes isopropanol per original amount of Triazol reagent used, and the sample centrifuged at room temperature for 10 minutes at 12,000×G. The supernatant was discarded, the pellet washed with 70% ethanol and then centrifuged at room temperature for 5 minutes at 12,000×G. Finally the 70% ethanol was removed and the centrifuge tube was let stand to dry in an inverted position. The resulting RNA pellet was resuspended in 100 µl water (1 µl per mg of original tissue weight) and heated to 55° C. until completely dissolved.

The RNA samples were then treated with DNAse to remove DNA. 28 µl of 5×reverse transcriptase buffer (Life Technologies, Gaithersburg, Md.), 10 µl 0.1 M DTT, and 5 units RNAguard per 100 mg starting tissue (Pharmacia Biotech, Uppsala, Sweden) and 1 unit RNase-free DNase I (Pharmacia Biotech) per 100 mg starting tissue were added to the resuspended RNA samples. The reaction mixture was incubated at 37° C. for 20 minutes. The total RNA concentration was quantified by measuring $OD_{260}$ of a 100-fold dilution and the samples stored at −20° C.

Poly-adenylated mRNA was isolated from the total RNA preparations using magnetic bead mediated oligo-dT detection with the Dynabeads mRNA Direct Kit from Dynal (Oslo, Norway) as directed by the manufacturer. The poly-adenylated RNA was harvested in a small volume of water, quantified by $OD_{260}$ measurement, and stored at −20° C.

cDNA was synthesized from the poly-adenylated RNA as follows. The poly $A^+$ RNA was mixed with 50 ng random hexamers (50 ng/µl) in 10 µl of water. The mixture was heated to 70° C. for 10 minutes, quick chilled in ice-water slurry, and kept on ice for 1–2 minutes. The condensate was collected by centrifugation in a microfuge for 10 seconds.

The first-strand synthesis was carried out by adding a reaction mixture of 4 µl 5×first strand buffer (from the BRL kit), 2 µl 100 mM DTT, 1 µl 10 mM dNTP mix, and 2 µl water to the primer-annealed RNA. The reaction mixtures were incubated at 37° C. for 2 minutes, 1 µl of Superscript II (BRL) (following manufacturer's recommendations) was added, and the reactions were then incubated at 37° C. for 1 hour.

To synthesize the second cDNA strand, the samples were placed on ice, 30 µl of 5×Second strand buffer, 90 µl of cold water, 3 µl of 10 mM dNTP, 1 µL (10 units) of *E. coli* DNA ligase (BRL), 4 µl (40 units) of *E. coli* DNA polymerase (BRL), and 1 µl (3.5 units) of *E. coli* RNase H (BRL) were added to the tubes, and the reactions were incubated for 2 hours at 16° C. The resulting cDNA was then incubated with 2 µl of T4 DNA polymerase (5 units) at 16° C. for 5 minutes.

The resulting cDNA was dephosphorylated with Arctic Shrimp Alkaline Phosphatase ("SAP"; obtained from USB); 20 µl 10×SAP buffer, 25 µl of water, and 5 µl (5 units) of SAP were added to the reaction mixtures and incubated at 37° C. for 30 minutes.

The cDNA was extracted with phenol-chloroform, chloroform-isoamyl alcohol, precipitated from the aqueous phase by addition of NaOAc to 0.3 M, 20 µg glycogen, and 2 volumes of ethanol, incubation at −20° C. for 10 minutes, and collected by centrifugation at 1 4,000×g for 10 minutes. The supernatant was removed and the pellet washed with 75% ethanol, resuspended in TE, and the cDNA quantitated.

For subsequent QEA processing, 75 ng cDNA was transferred to a separate tube, resuspended in TE to a concentration 600 ng/ml, and stored at −20° C.

QEA analysis was performed as disclosed in PCT Publication WO 97/15690 dated May 1, 1997. Restriction enzyme pairs for the identified genes are listed in Tables I and II. Adapter molecules for the QEA analysis were prepared from linker and primer oligonucleotides. One set of primers were labeled with FAM fluorescent label and one set were labeled with a biotin moiety. The adapters were prepared by mixing the linker and primer oligonucleotides together in water at a concentration ratio of 1:20 (linker to primer) with the primer at a total concentration of 50 pm/µl. The mixture was incubated at 50° C. for 10 minutes and then allowed to cool slowly to room temperature to anneal the linkers and primers. The adapters were stored at −20° C.

The QEA reactions were performed using an automated QEA procedure. Reactions were preformed in a standard 96 well thermal cycler format using a Beckman Biomek 2000 robot (Beckman, Sunnyvale, Calif.). The 3 cDNA samples were analyzed in triplicate with corresponding restriction enzyme pairs. All steps were performed by the robot, including solution mixing, from user provided stock reagents, and temperature profile control.

The RE/ligase reaction contained the following components per reaction:
1. 1 U each restriction enzyme (New England Biolabs, Beverly, Mass.)
2. 1 µl of each annealed adapter prepared as above (10 pm)
3. 0.1 µl T4 DNA ligase [1 U/µl] (Life Technologies (Gaithersburg, Md.)
4. 1 µl ATP (Life Technologies, Gaithersburg, Md.)
5. 5 ng of the prepared cDNA
6. 1.5 µl 10×NEB 2 buffer from New England Biolabs (Beverly, Mass.)
7. 0.5 µl of 50 mM $MgCl_2$
8. Water to bring total volume to 10 µl and transfer to thermal cycler.

The robot performed the RE/ligation reaction in a PTC-100 Thermal Cycler equipped with a mechanized lid from MJ Research (Watertown, Mass.) with the following temperature profile: 15 minutes at 37° C. ramp down 21° C. in 5 minutes, 16° C. for 30 minutes, 37° C. for 10 minutes, and 65° C. for 10 minutes.

The PCR reaction mix contained the following components per reaction:
1. 10 µl 5×E-Mg (300 mM Tris-HCl pH 9.0, 75 mM $(NH_4)_2SO_4$)
2. 100 pm of primers (one set labeled with FAM; the other set labeled with biotin).
3. 1 µl 10 mM dNTP mix (Life Technologies, Gaithersburg, Md.)
4. 2.5 U of 50:1 Taq polymerase (Life Technologies, Gaithersburg, Md.): Pfu polymerase (Stratagene, La Jolla, Calif.)
5. Water to being volume to 35 µl per PCR reaction The PCR mix was heated to 72° C. and 35 µl was transferred to each digestion/ligation reaction. The PTC-100 Thermal Cycler then performed the PCR reaction with a thermal profile of 72° C. for 10 minutes, 15 cycles of 95° C. for 30 seconds and 68° C. for 1minute, and then 72° C. for 10 minutes, and finally holding the reactions at 4° C.

Before further analysis, the QEA products were subjected to a post-PCR clean up protocol as follows:
1. Streptavidin magnetic beads (Catalog No. MSTR0510 of CPG, Lincoln Park, N.J.) were prepared (3 µl of beads for every 5 µl of QEA reaction product) by pre-washing beads in 10 µl binding buffer (5 M NaCl, 10 mM Tris, pH 8.0, 1 mM EDTA) per 5 µl original volume of QEA reaction product.
2. 10 µl of washed beads were dispensed in a 96 well FALCONJ TC plate for every QEA sample processed.
3. QEA products were added to the beads, mixed well and incubated for 30 minutes at 50° C.
4. The sample volume was made 100 µl with binding buffer, the plate placed on a 96 well magnetic particle concentrator, and the beads allowed to migrate for 5 minutes.
5. The liquid was then removed, and 200 µl washing buffer (10 mM Tris, pH 7.4, 10 mM EDTA) added per well.
6. Washing step 5 was repeated.

For analysis, the beads were resuspended in 5 µl loading buffer (80% deionized formamide, 20% 25 mM EDTA, pH 8.0, 50 mg/ml Blue dextran) per 5 µl of beads, and the supernatant was then analyzed by electrophoresis on an ABI 377 (Applied Biosystems, Inc.) automated sequencer under denaturing conditions using the Gene Scan software (ABI) for analysis. The GeneScan 500 ROX ladder was diluted 1:10 in loading buffer and analyzed as a size control.

Oligonucleotide poisoning was performed to confirm the identity of the differentially expressed fragments. Essentially, an unlabeled oligonucleotide having a nucleotide sequence able to hybridize to the identified sequence (and prevent amplification with the labeled primers) was included in a PCR reaction using the QEA reaction products as substrate.

Specifically, for the oligonucleotide poisoning, each reaction mixture contained 1 µl of a 1:100 dilution of the QEA reaction products, 5 µl TB 2.0 (500 mM Tris-HCl pH 9.15, 160 mM $(NH_4)_2SO_4$, 20 mM $MgCl_2$), 2 µl 10 mM equimolar mixture of all four dNTPs, 0.2 µl each primers (100 pm/ml), 2 µl CHAG poisoning primer (1000 pm/ml), 1 µl 5 M betaine, 1 µl NEB 2 buffer (10 mM Tris-HCl, 10 mM $MgCl_2$, 50 mM NaCl, 1 mM DTT (pH 7.9 at 25EC), 0.25 µl 25 U/ml of a 16:1 mixture of Klentaq:pfu, and 38 µl water.

The following PCR temperature protocol was performed in a thermal cycler for 13 cycles:
96° C. for 30 seconds;
57° C. for 1 minute;
72° C. for 2 minutes.

The amplified products were held at 4° C. and then analyzed as described above on the automatic sequencer.

(b) Experimental Results

At two weeks post surgery there was a significant increase in the ventricle weight:body weight ratio (4.19:0.52 mg/g) compared to the sham surgery group (2.59:0.52 mg/g), with up to a 60% increase in ventricle mass.

QEA was performed on pressure overloaded hearts, sham surgery hearts, and non-operated hearts and comparisons of expression profiles were made in silico between the pressure overload and sham surgery hearts and the pressure overload and non-operated hearts. The first comparison controls for differences induced by surgery, the second allows for the detection of all surgery-related changes in gene expression. Bands representing genes differentially expressed in both comparisons were confirmed for gene identity by oligonucleotide poisoning of the identified differentially expressed fragments with matches in the database and direct cloning and sequencing of bands with no matches from the publicly available database.

A total of 12,000 gene fragments per sample group were examined for expression levels, which represents approximately 6,000 unique expressed sequences in the heart. The comparison between the pressure overload hearts and the sham surgery hearts yielded 74 differences (0.6%) while the pressure overload versus non-operated hearts gave 117 differences (1.0%). When these two analyses are combined, the number of gene fragments differentially expressed between the pressure overload hearts and both the sham surgery and normal hearts is only 39 fragments (0.3%). Oligonucleotide poisoning, cloning and sequence analysis of the differentially expressed bands revealed 32 differentially expressed genes (See Tables I and II).

Genes identified by QEA (Tables I & II) include those known to be regulated in cardiac hypertrophy (ANF, ANF precursor, ANP, α skeletal actin, MLC2, α and β MHC, and fibronectin) and genes not previously implicated in hypertrophy (CH-1, CH-2, CH-3, CH-4, CH-5, CH-6, CH-7, CH-8, CH-9, and α-Enolase, Atrial Natriuretic Peptide (ANP), Antizyme Inhibitor, Biglycan, Cytochrome Oxidase I, Cytochrome Oxidase II, Cyclin G, D-binding protein, Desmin, Fibrillin, Laminin γ-1, p85, Preproenkephalin, Protein Kinase C-Binding Protein β15 and genes encoding 5.8S, 18S and 28S rRNAs). The identification of genes previously associated with cardiac hypertrophy provides biological validation of QEA. Prominent among the known genes are myocyte-specific transcripts that represent re-expression of a fetal molecular phenotype. These include ANP α-skeletal actin, and myosin heavy chain isoform switching (Samuel, et al., *J. Clin. Invest.* 88:1737–1746 (1991)). Induction of the fetal isoform of fibronectin in cardiac non-myocytes and smooth muscle has also been described (Chapman et al., *Circ. Res.* 67:787–794 (1990)), and is consistent with the fibronectin induction detected by QEA (Table I, FIG. 2).

TABLE I

| Gene | Fragment | Enzyme Pair | % Difference | N-Fold Difference | Figure No. | SEQ. ID (DNA) |
|---|---|---|---|---|---|---|
| (CH1) Homologous to human Short-chain alcohol dehydrogenase and mouse amyloid beta-peptide binding protein | i0a0-114.7 | BglII/Acc651 | −35.44 | −1.5 | See FIG. 2 | SEQ. ID NO: 1 |
| (CH2) Homologous to mouse α-1 Collagen Type III | b0p0-206.1 | AgeI/BstYI | +282.85 | +3.8 | See FIG. 3 | SEQ. ID NO: 2 |
| (CH3) Homologous to mouse α-1 Collagen Type IV | | | +226.90 | +3.3 | See FIG.4 | SEQ. ID NO: 3 |
| (CH4) Homologous to chicken Collagen Type XIV | 10a0-121 | BspEI/Acc65 I | +84.03 | +1.8 | See FIG. 5 | SEQ. ID NO: 4 |
| (CH5) Homologous to human 13kD DAP | a0e1-67 | Acc651/EaeI | +264.17 | +3.6 | See FIG. 6 | SEQ. ID NO: 5 |
| (CH6) Homologous to mouse and human Gelsolin | g0c0-142.1 | BamHI/ApaL I | +327.35 | +4.3 | See FIG. 7 | SEQ. ID NO: 6 |
| (CH7) Homologous to mouse Osteonectin | p0s0-127.4 | BasYI/HindII I | +158.80 | +2.6 | See FIG. 8 | SEQ. ID NO: 7 |
| (CH8) Homologous mouse Transglutaminase | g0s0-145 | BamHI/HindI II | +98.33 | +2.0 | See FIG. 9 | SEQ. ID NO: 8 |
| (CH9) Homologous to mouse and human Zyxin | w0c0-266.2 | NheI/KasI | +1983.33 | +20.8 | See FIG. 10 | SEQ. ID NO: 9 |

TABLE II

| Gene | Fragment | Enzyme Pair | % Difference | N-Fold Difference | GB Accession No. |
|---|---|---|---|---|---|
| Rattus sp. α-Enolase | | | +120.02 | +2.2 | Gber h35207 |
| Rat Antizyme Inhibitor | m0 0 122.7 | BopHI/HindIII | +101.29 | +2.0 | D50734 |
| *Rattus norvegicus* Biglycan | i0m0-168.6 | BglII/BspHi | +243.64 | +3.4 | U17834 |
| | i010-136 | BglII/SalI | | | |
| | i0p0-136.2 | BspEI/BstYI | | | |
| | i0n0-95 | BglII/BsrGI | | | |
| | i0n0-133 | BglII/BsrGI | | | |
| | i031-189.7 | BglII/EaeI | | | |
| | p0e1-190 | BstYI/EaeI | | | |
| Rat Cytochrome Oxidase 1 | m0s0-203.2 | BspHI/HingIII | +231.90 | +3.3 | J01435 |
| *Rattus norvegicus* Cytochrome Oxidase II | n0r0-387.3 | BsrGI/EcoRI | +202.30 | +3.0 | J01434 |
| *Rattus norvegicus* Cyclin G | gli0-329 | BglII/XbaI | +235.23 | +3.4 | X70871 |
| Rat D-binding protein | | | +85.87 | +1.8 | J03179 |
| *Rattus norvegicus* Desmin | p0r0-259 | BstYI/EcoRI | −45.39 | −1.8 | X73524 |
| Fibrillin | i0m0-148.3 | BglII/BspHI | | | L19896 |
| *Rattus norvegicus* Laminin α-1 | p0r0-294 | BstYI/EcoRI | +258.95 | +3.6 | X94551 |
| Rat Preproenkephalin | m0n0-271.1 | BapHI/BsrGI | +235.57 | +3.4 | K02805 |
| *Rattus norvegicus* Protein kinase C-binding protein α15 | g0s0-255.4 | BamHI/HindIII | −81.00 | −5.3 | U48248 |
| *Rattus norvegicus* p85 | R0s0-44.7 | EcoRI/HingIII | +332.90 | +4.3 | U42581 |
| Human 28S rRNA gene | | | −80.30 | −5.1 | M11167 |
| *R. norvegicus* genes for 5.8S, 18S, and 28S rRNAs | | | −69.21 | −3.2 | V01270 |
| Rat α-Skeletal Actin | bli0-199 | BsrFI/BglII | +265.50 | +3.7 | J00692 |
| | I0e1-189.7 | BglII/EaeI | | | |
| | p0e1-190 | BstYI/EaeI | | | |
| | b1p0-379.7 | BsrFI/BstYI | | | |
| | m0n0-420.3 | BspHI/BsrGI | | | |
| | m0v0-254 | BsPHI/NgnoMI | | | |
| Rat ANF | | | +605.72 | +7.1 | K02062 |
| Rat ANF precursor | | | +605.72 | +7.1 | X00665 |
| Rat Atrial Natriuretic Peptide (ANP) | bli0-171.8 | BsrFI/BglII | | | X01118 |
| | i0a0-136 | BglII/Acc651 | +471.76 | +5.7 | |
| Rat MLC2 | | | +57.36 | +1.6 | M11851 |

TABLE II-continued

| Gene | Fragment | Enzyme Pair | % Difference | N-Fold Difference | GB Accession No. |
|---|---|---|---|---|---|
| α-Cardiac MHC | p0x0.49.5 | BstYI/ | | | K01464 |
| α-Cardiac MHC | bli0-427.4 | BsrBI/BglII | | | K01463 |
| Rat Fibronectin | i0r0-131.9 | BglII/EcoRI | +276.79 | +3.8 | X15906 |

Increased collagen III and IV mRNA represents changes in both fibrillar and basement membrane components during pressure overload (SchÖnherr, et al., *J. Biol. Chem.* 270:2776–2783 (1995); Heimer et al., *J. Mol. Cell. Cardiol.* 27:2191–2198 (1995)).

Detectable changes in steady state expression by QEA ranged from −1.5 for weak repression of CH-1 to 20-fold induction of CH-9. To provide independent confirmation and quantitative validation of QEA, Northern blotting was used to measure changes in steady state mRNA levels. Induction values for ANP, p85, biglycan, laminin, desmin, and α-skeletal actin were plotted against QEA results (FIG. 1) to illustrate that Northorn analysis confirmed the QEA results. Desmin, p85 and laminin showed the largest difference between Northern and QEA values, either due to errors inherent in generating reproducible and normalized quantitative Northern data, or stochastic errors due to the sample size used for the two techniques. Nevertheless, p85 and laminin did show induction by Northern analysis, as did the remaining genes, with a 50% to 3-fold difference in the value obtained. This comparison suggests that QEA does not introduce a systematic bias in either over- or underestimating changes in mRNA levels.

Numerous genes have been described in association with the molecular phenotype of cardiac hypertrophy. However, QEA of POL ventricles identified a relatively small number of differences. Part of this discrepancy may be due to model-specific sensitivity in detecting expression. To determine if QEA potentially missed genes due to an incomplete set of subsequences, expression below the limit of sensitivity, or simply did not score differential expression, a directed search of the QEA database was performed for five genes. Numerous fragments corresponding to TGF-β1, collagen-I, angiotensin converting enzyme, angiotensinogen, and endothelin-1 were identified based on length and end restriction sites. None of the fragments identified in the directed query were identified by QEA as differentially expressed either by software or by visual inspection. This analysis is consistent with the small number of differences found by QEA and suggests that a representative population of cDNA fragments is being sampled for expression differences.

The changes in gene expression found by QEA represent re-expression of a fetal phenotype in myocytes and non-myocytes, extracellular matrix expression, and cell cycle-related genes. A variety of cell types are involved in the tissue response to POL, some of which may be minor constituents of the myocardium. It is therefore likely that there are significant changes in expression occurring below the current sensitivity of QEA. For instance, if, in a cell type representing 10% of the total population sampled, a gene undergoes a 10-fold change which is at a constant and equivalent level in the other 90% the cells, the total change observed by QEA would be less than twofold. If the expression levels of that gene are even higher in the non-modulating cells then the overall difference is further diminished, making the study of more complex tissues by expression analysis difficult without sophisticated cell type-specific dissection or purification. Therefore, it is very likely that some of the modest differences found by QEA in the total heart will be due to large differences in a subset of cells within the myocardium.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publication are cited herein, the disclosures of which are incorporated by reference in their entireties.

What is claimed is:

1. An isolated nucleic acid comprising a nucleotide sequence selected from the group consisting of SEQ ID NO:3, SEQ ID NO:4, SEQ ID NO:5, SEQ ID NO:6, SEQ ID NO:7, SEQ ID NO:8 and SEQ ID NO:9.

2. An isolated nucleic acid comprising a nucleotide sequence that is a full complement of a sequence selected from the group consisting of SEQ ID NO:3, SEQ ID NO:4, SEQ ID NO:5, SEQ ID NO:6, SEQ D NO:7, SEQ ID NO:8 and SEQ ID NO:9.

3. The isolated nucleic acid of claim 1, wherein said nucleotide sequence is-SEQ ID NO:3.

4. The isolated nucleic acid of claim 1, wherein said nucleotide sequence is SEQ ID NO:4.

5. The isolated nucleic acid of claim 1, wherein said nucleotide sequence is SEQ ID NO:5.

6. The isolated nucleic acid of claim 1, wherein said nucleotide sequence is SEQ ID NO:6.

7. The isolated nucleic acid of claim 1, wherein said nucleotide sequence is SEQ ID NO:7.

8. The isolated nucleic acid of claim 1, wherein said nucleotide sequence is SEQ ID NO:8.

9. The isolated nucleic acid of claim 1, wherein said nucleotide sequence is SEQ ID NO:9.

10. The isolated nucleic acid of claim 2, wherein said nucleotide sequence is fully complementary to SEQ ID NO:3.

11. The isolated nucleic acid of claim 2, wherein said nucleotide sequence is fully complementary to SEQ ID NO:4.

12. The isolated nucleic acid of claim 2, wherein said nucleotide sequence is fully complementary to SEQ ID NO:5.

13. The isolated nucleic acid of claim 2, wherein said nucleotide sequence is fully complementary to SEQ ID NO:6.

14. The isolated nucleic acid of claim 2, wherein said nucleotide sequence is fully complementary to SEQ ID NO:7.

15. The isolated nucleic acid of claim 2, wherein said nucleotide sequence is fully complementary to SEQ ID NO:8.

16. The isolated nucleic acid of claim 2, wherein said nucleotide sequence is fully complementary to SEQ ID NO:9.

17. An isolated nucleic acid fragment of a nucleic acid selected from the group consisting of SEQ ID NO:4, SEQ ID NO:5 and SEQ ID NO:8, wherein the fragment consists of at least 25 contiguous nucleotides of the nucleic acid; or complement thereof.

18. The isolated nucleic acid fragment of claim 16, wherein said fragment is a fragment of SEQ ID NO:4, or a full complement thereof.

19. The isolated nucleic acid of claim 16, wherein said fragment is a fragment of SEQ ID NO:5; or a full complement thereof.

20. The isolated nucleic acid of claim 16, wherein said fragment is a fragment of SEQ ID NO:8; or a full complement thereof.

21. A probe suitable for detecting cardiac hypertrophy in a tissue sample, wherein the probe consists essentially of a nucleic acid fragment of a nucleic acid selected from the group consisting of SEQ ID NO:4, SEQ ID NO:5 and SEQ ID NO:8, wherein the fragment consists of at least 25 contiguous nucleotides of the nucleic acid; or a full complement thereof.

22. The probe of claim 21, wherein the nucleic acid is SEQ ID NO:4.

23. The probe of claim 21, wherein the nucleic acid is SEQ ID NO:5.

24. The probe of claim 21, wherein the nucleic acid is SEQ ID NO:8.

25. A method of detecting cardiac hypertrophy from a tissue sample, comprising hybridizing the probe of claim 21 with nucleic acid in the sample, said hybridization is indicative of the presence of SEQ ID NO:4, SEQ ID NO;5 or SEQ ID NO:8.

26. A method of detecting cardiac hypertrophy from a tissue sample, comprising hybridizing the probe of claim 22 with nucleic acid in the sample, said hybridization is indicative of the presence of SEQ ID NO:4.

27. A method of detecting cardiac hypertrophy from a tissue sample, comprising hybridizing the probe of claim 23 with nucleic acid in the sample, said hybridization is indicative of the presence of SEQ ID NO:5.

28. A method of detecting cardiac hypertrophy from a tissue sample, comprising hybridizing the probe of claim 24 with nucleic acid in the sample, said hybridization is indicative of the presence of SEQ ID NO:8.

* * * * *

SEQUENCE LISTING

```
<160> NUMBER OF SEQ ID NOS: 32

<210> SEQ ID NO 1
<211> LENGTH: 114
<212> TYPE: DNA
<213> ORGANISM: Rattus sp.
<220> FEATURE:
<221> NAME/KEY: modified_base
<222> LOCATION: (1)..(114)
<223> OTHER INFORMATION: "n" represents a, t, c, g, other or unknown

<400> SEQUENCE: 1
ggtacctggn tggccaagaa gttgcgnant ttgtntggna gagtggtaag cagtggggtg      60
gcaaacagac ctggagcaat tgttaccaca cggatgccta taggagcnag atct          114

<210> SEQ ID NO 2
<211> LENGTH: 198
```

```
<212> TYPE: DNA
<213> ORGANISM: Rattus sp.
<220> FEATURE:
<221> NAME/KEY: modified_base
<222> LOCATION: (1)..(198)
<223> OTHER INFORMATION: "n" represents a, t, c, g, other or unknown

<400> SEQUENCE: 2
rgatccaggg aatcctgcag ttccaggagg accaggggga cctggttgcc cgtcactgcc      60
ccgagcacca tcattgcctc gagcacctgc ggctccagga agacctggtc gtcctcgctc     120
accaggagcc cctctgggac ccatggggcc aggagctccg ttgtctcccg gaagaccgtt     180
ttcacccttc aatccagg                                                   198

<210> SEQ ID NO 3
<211> LENGTH: 270
<212> TYPE: DNA
<213> ORGANISM: Rattus sp.
<220> FEATURE:
<221> NAME/KEY: modified_base
<222> LOCATION: (1)..(270)
<223> OTHER INFORMATION: "n" represents a, t, c, g, other or unknown

<400> SEQUENCE: 3
tccggagtgg acagccagta ggagtagtcg ttcctggagg cgaagttgca gacgttgttg      60
atgttgcaga agaggaaggg catggtgctg aacttgcgca gacagctgcc agccgtaccc     120
aagtcctgac catgggcccg ctcgtttcct tggacataga gcagagagta cccatggtaa     180
agaattttgg tccctggggg acacagcggg tcatctcacn gtctgactat gcctggtcac     240
aaggaagcca tggtccacag atggggtacc                                      270

<210> SEQ ID NO 4
<211> LENGTH: 121
<212> TYPE: DNA
<213> ORGANISM: Rattus sp.
<220> FEATURE:
<221> NAME/KEY: modified_base
<222> LOCATION: (1)..(121)
<223> OTHER INFORMATION: "n" represents a, t, c, g, other or unknown

<400> SEQUENCE: 4
ggtaccttcn atttgttccc atgctatcnn atccntaagg atgccctggt ttcccagcca      60
ncnnagtgtc tgcacccngn aggattgcct gctgnctntn cnntgacttt tctgttccgg     120
a                                                                     121

<210> SEQ ID NO 5
<211> LENGTH: 66
<212> TYPE: DNA
<213> ORGANISM: Rattus sp.
<220> FEATURE:
<221> NAME/KEY: modified_base
<222> LOCATION: (1)..(66)
<223> OTHER INFORMATION: "n" represents a, t, c, g, other or unknown

<400> SEQUENCE: 5
yggccacggc ggcctgcggg gcntnancgg gttttcctca gggcaaatga tataaggctc      60
ggtacc                                                                66

<210> SEQ ID NO 6
<211> LENGTH: 143
<212> TYPE: DNA
<213> ORGANISM: Rattus sp.
<220> FEATURE:
```

<221> NAME/KEY: modified_base
<222> LOCATION: (1)..(143)
<223> OTHER INFORMATION: "n" represents a, t, c, g, other or unknown

<400> SEQUENCE: 6

```
gtgcacacac actatagttt tcctgcttgt ccttnngttc tctctgggag atggacaacc      60
ctcaaaggca ctgattgntg acattnntag ctctgntcct tactcaggca gccagctcag     120
ccaaggcccg gtccaaggga tcc                                             143
```

<210> SEQ ID NO 7
<211> LENGTH: 127
<212> TYPE: DNA
<213> ORGANISM: Rattus sp.

<400> SEQUENCE: 7

```
rgatcccaag tcacagcatt ttcccacgta actcgactct gaggccatag cctatccaca      60
gcctcctcgt cccctgcacc gcccagtgtc tcactggctg tgttggagac gggaattgca     120
taagctt                                                               127
```

<210> SEQ ID NO 8
<211> LENGTH: 147
<212> TYPE: DNA
<213> ORGANISM: Rattus sp.
<220> FEATURE:
<221> NAME/KEY: modified_base
<222> LOCATION: (1)..(147)
<223> OTHER INFORMATION: "n" represents a, t, c, g, other or unknown

<400> SEQUENCE: 8

```
aagcttgcac agatcaaaag aaatggaacc gtgtggggac aaggcaaata aaaaaactca      60
cggtgcnatt ctcnncataa agcgaaacgg tttaaatgca gcagtgtgan ttcttcccan     120
ttccttctct gggatttcag gggatcc                                         147
```

<210> SEQ ID NO 9
<211> LENGTH: 266
<212> TYPE: DNA
<213> ORGANISM: Rattus sp.
<220> FEATURE:
<221> NAME/KEY: modified_base
<222> LOCATION: (1)..(266)
<223> OTHER INFORMATION: "n" represents a, t, c, g, other or unknown

<400> SEQUENCE: 9

```
gtgcacggac tgnaggctgt gctcgggcca gtggtgactg catttgccac aggactcatt      60
tactgccacg ctctgcctct ganggtnntc cangtncnnn annanntnan nggtnanntn     120
ntncaaatnt tncaactncn tnaaggtnaa ngggnctggg ctncaagaga acgtanctgg     180
ttttggtttt gagatggtgg aggcagtggg tgctgcttct cttgaactag gggcttctcc     240
ttctgctgag cataggtgaa gctagc                                          266
```

<210> SEQ ID NO 10
<211> LENGTH: 114
<212> TYPE: DNA
<213> ORGANISM: Rattus sp.
<220> FEATURE:
<221> NAME/KEY: modified_base
<222> LOCATION: (1)..(114)
<223> OTHER INFORMATION: "n" represents a, t, c, g, other or unknown

<400> SEQUENCE: 10

```
agatctngct cctataggca tccgtgtggt aacaattgct ccaggtctgt ttgccacccc      60
```
actgcttacc actctnccan acaaantncg caacttcttg gccanccagg tacc         114

<210> SEQ ID NO 11
<211> LENGTH: 114
<212> TYPE: DNA
<213> ORGANISM: Mus sp.

<400> SEQUENCE: 11
agatctggct cctacaggca tccgtgtggt aacaattgcg ccaggtttgt ttgccacccc   60
actgcttacc acccttccag agaaagtgcg aaacttcttg gccagccagg tacc         114

<210> SEQ ID NO 12
<211> LENGTH: 113
<212> TYPE: DNA
<213> ORGANISM: Rattus sp.
<220> FEATURE:
<221> NAME/KEY: modified_base
<222> LOCATION: (1)..(113)
<223> OTHER INFORMATION: "n" represents a, t, c, g, other or unknown

<400> SEQUENCE: 12
gatctngctc ctataggcat ccgtgtggta acaattgctc caggtctgtt tgccacccca   60
ctgcttacca ctctnccana caaantncgc aacttcttgg ccanccaggt acc          113

<210> SEQ ID NO 13
<211> LENGTH: 113
<212> TYPE: DNA
<213> ORGANISM: Homo sapiens

<400> SEQUENCE: 13
gatctggctc ccataggtat ccgggtgatg accattgccc caggtctgtt tggcacccca   60
ctgctgacca gcctcccaga gaaagtgtgc aacttcttgg ccagccaagt gcc          113

<210> SEQ ID NO 14
<211> LENGTH: 197
<212> TYPE: DNA
<213> ORGANISM: Rattus sp.

<400> SEQUENCE: 14
cctggattga agggtgaaaa cggtcttccg ggagacaacg gagctcctgg ccccatgggt   60
cccagagggg ctcctggtga gcgaggacga ccaggtcttc ctggagccgc aggtgctcga   120
ggcaatgatg gtgctcgggg cagtgacggg caaccaggtc cccctggtcc tcctggaact   180
gcaggattcc ctggatc                                                  197

<210> SEQ ID NO 15
<211> LENGTH: 197
<212> TYPE: DNA
<213> ORGANISM: Mus sp.

<400> SEQUENCE: 15
cctggactga agggtgaaaa tgttcttcca ggagacaacg gagctcctgg ccccatgggt   60
cctagagggg ctcctggtga gcgaggacga ccaggccttc ctggagctgc aggtgctcga   120
ggcaatgatg gtgctcgggg cagtgatggg caacctggtc ccctggccc tcctggaact    180 gcaggattcc ctggatc                                                  197

<210> SEQ ID NO 16
<211> LENGTH: 270
<212> TYPE: DNA

<213> ORGANISM: Rattus sp.
<220> FEATURE:
<221> NAME/KEY: modified_base
<222> LOCATION: (1)..(270)
<223> OTHER INFORMATION: "n" represents a, t, c, g, other or unknown

<400> SEQUENCE: 16

```
ggtaccccat ctgtggacca tggcttcctt gtgaccaggc atagtcagac ngtgagatga    60
cccgctgtgt cccccaggga ccaaaattct ttaccatggg tactctctgc tctatgtcca   120
aggaaacgag cgggcccatg gtcaggactt gggtacggct ggcagctgtc tgcgcaagtt   180
cagcaccatg cccttcctct tctgcaacat caacaacgtc tgcaacttcg cctccaggaa   240
cgactactcc tactggctgt ccactccgga                                    270
```

<210> SEQ ID NO 17
<211> LENGTH: 269
<212> TYPE: DNA
<213> ORGANISM: Mus sp.

<400> SEQUENCE: 17

```
ggtaccccat ctgtggacca tggcttcctt gtgaccaggc atagtcagac aacagatgac    60
ccactgtgtc ccccagggac caaaattctt taccatggat actctctgct ctatgtccaa   120
ggcaacgagc gtgcccacgg gcaggacttg ggtacgctg gcagctgcct gcgtaagttc   180
agcaccatgc cctttctctt ctgcaacatc aacaacgtct gcaacttcgc ctccaggaac   240
gactactctt actggctgtc cacgccaga                                     269
```

<210> SEQ ID NO 18
<211> LENGTH: 270
<212> TYPE: DNA
<213> ORGANISM: Artificial Sequence
<220> FEATURE:
<223> OTHER INFORMATION: Description of Artificial Sequence: Consensus
      sequence
<221> NAME/KEY: modified_base
<222> LOCATION: (1)..(270)
<223> OTHER INFORMATION: "n" represents a, t, c, g, other or unknown

<400> SEQUENCE: 18

```
ggtaccccat ctgtggacca tggcttcctt gtgaccaggc atagtcagac nnnnagatga    60
cccnctgtgt cccccaggga ccaaaattct ttaccatggn tactctctgc tctatgtcca   120
aggnaacgag cgngcccang gncaggactt gggtacggct ggcagctgnc tgcgnaagtt   180
cagcaccatg cccttnctct tctgcaacat caacaacgtc tgcaacttcg cctccaggaa   240
cgactactcn tactggctgt ccacnccnga                                    270
```

<210> SEQ ID NO 19
<211> LENGTH: 121
<212> TYPE: DNA
<213> ORGANISM: Homo sapiens

<400> SEQUENCE: 19

```
ggtaccttca atgtgtttcc atgttaccaa ctccataaag atgccctggt ttcccagcca    60
accaggtact tgcacccaga aggattgccc tccgactaca caatcagttt tctattccgg   120
a                                                                   121
```

<210> SEQ ID NO 20
<211> LENGTH: 64
<212> TYPE: DNA
<213> ORGANISM: Rattus sp.

```
<220> FEATURE:
<221> NAME/KEY: modified_base
<222> LOCATION: (1)..(64)
<223> OTHER INFORMATION: "n" represents a, t, c, g, other or unknown

<400> SEQUENCE: 20
ggccacggcg gcctgcgggg cntnancggg ttttcctcag ggcaaatgat ataaggctcg    60
gtac                                                                64

<210> SEQ ID NO 21
<211> LENGTH: 65
<212> TYPE: DNA
<213> ORGANISM: Homo sapiens

<400> SEQUENCE: 21
ggccacggcg gtctccgagg ctatctacgg gttttttttca ggacaaatga tgcgaagggt   60
ggtac                                                               65

<210> SEQ ID NO 22
<211> LENGTH: 66
<212> TYPE: DNA
<213> ORGANISM: Artificial Sequence
<220> FEATURE:
<223> OTHER INFORMATION: Description of Artificial Sequence: Consensus
      sequence
<221> NAME/KEY: modified_base
<222> LOCATION: (1)..(66)
<223> OTHER INFORMATION: "n" represents a, t, c, g, other or unknown

<400> SEQUENCE: 22
ggccacggcg gnctncgngg cnntnnncgg gttttnntca ggncaaatga tnnnaaggnt    60 nggtac                                                              66

<210> SEQ ID NO 23
<211> LENGTH: 143
<212> TYPE: DNA
<213> ORGANISM: Rattus sp.
<220> FEATURE:
<221> NAME/KEY: modified_base
<222> LOCATION: (1)..(143)
<223> OTHER INFORMATION: "n" represents a, t, c, g, other or unknown

<400> SEQUENCE: 23
ggatcccttg gaccgggcct tggctgagct ggctgcctga gtaagganca gagctannaa    60
tgtcancaat cagtgccttt gagggttgtc catctcccag agagaacnna aggacaagca   120
ggaaaactat agtgtgtgtg cac                                           143

<210> SEQ ID NO 24
<211> LENGTH: 141
<212> TYPE: DNA
<213> ORGANISM: Mus sp.

<400> SEQUENCE: 24
ggatcctttg gaccgggcct tggctgagct ggctgcctga gtaaggacca agccatcaat    60
gtcaccaatc agtgcctttg agggttgtcc atctcccaaa gacatcatat ggcaagcagg   120
aaaactatga tgtgtgcgcg c                                             141

<210> SEQ ID NO 25
<211> LENGTH: 143
<212> TYPE: DNA
<213> ORGANISM: Artificial Sequence
<220> FEATURE:
```

```
<223> OTHER INFORMATION: Description of Artificial Sequence: Consensus
      sequence
<221> NAME/KEY: modified_base
<222> LOCATION: (1)..(143)
<223> OTHER INFORMATION: "n" represents a, t, c, g, other or unknown

<400> SEQUENCE: 25
ggatccnttg gaccgggcct tggctgagct ggctgcctga gtaagganca nagcnannaa      60
tgtcancaat cagtgccttt gagggttgtc catctcccan aganancnna nggncaagca     120
ggaaaactat nntgtgtgng cnc                                             143

<210> SEQ ID NO 26
<211> LENGTH: 127
<212> TYPE: DNA
<213> ORGANISM: Rattus sp.

<400> SEQUENCE: 26
agatcccaag tcacagcatt ttcccacgtt actcgactct gaggccatag cctatccaca      60
gcctcctcgt ccctgcacc gcccagtgtc tcactggctg tgttggaaac gggaattgca     120
taagctt                                                               127

<210> SEQ ID NO 27
<211> LENGTH: 147
<212> TYPE: DNA
<213> ORGANISM: Rattus sp.
<220> FEATURE:
<221> NAME/KEY: modified_base
<222> LOCATION: (1)..(147)
<223> OTHER INFORMATION: "n" represents a, t, c, g, other or unknown

<400> SEQUENCE: 27
ggatcccctg aaatcccaga gaaggaantg ggaagaantc acactgctgc atttaaaccg      60
tttcgcttta tgnngagaat ngcaccgtga gttttttttat ttgccttgtc cccacacggt    120
tccatttctt ttgatctgtg caagctt                                         147

<210> SEQ ID NO 28
<211> LENGTH: 146
<212> TYPE: DNA
<213> ORGANISM: Mus sp.

<400> SEQUENCE: 28
ggatcccctg aaatcccgga gaagagcctg ggaagaatca aactgatgca tttaacgcgt      60
tctgctttac acagaggatc gcaccgtgag ccgtgctatc tgtcctgtcc ccacacggtt     120
ctgtttcttt tggtctgtgc aagctt                                          146

<210> SEQ ID NO 29
<211> LENGTH: 147
<212> TYPE: DNA
<213> ORGANISM: Artificial Sequence
<220> FEATURE:
<223> OTHER INFORMATION: Description of Artificial Sequence: Consensus
      sequence
<221> NAME/KEY: modified_base
<222> LOCATION: (1)..(147)
<223> OTHER INFORMATION: "n" represents a, t, c, g, other or unknown

<400> SEQUENCE: 29
ggatcccctg aaatcccnga gaagnnnntg ggaagaantc anactgntgc atttaanncg      60
ttnngcttta nnnngagnat ngcaccgtga gnnntnnnat ntgncntgtc cccacacggt     120
tcnntttctt ttgntctgtg caagctt                                         147
```

```
<210> SEQ ID NO 30
<211> LENGTH: 265
<212> TYPE: DNA
<213> ORGANISM: Rattus sp.
<220> FEATURE:
<221> NAME/KEY: modified_base
<222> LOCATION: (1)..(265)
<223> OTHER INFORMATION: "n" represents a, t, c, g, other or unknown

<400> SEQUENCE: 30
ctagcttcac ctatgctcag cagaaggaga agcccctagt tcaagagaag cagcacccac      60
tgcctccacc atctcaaaac caaaaccagn tacgttctct tgnagcccag ncccnttnac     120
cttnangnag ttgnaanatt tgnannannt naccnntnan ntnntnnngn acntgganna     180
ccntcagagg cagagcgtgg cagtaaatga gtcctgtggc aaatgcagtc accactggcc     240
cgagcacagc ctncagtccg tgcac                                          265

<210> SEQ ID NO 31
<211> LENGTH: 267
<212> TYPE: DNA
<213> ORGANISM: Mus sp.

<400> SEQUENCE: 31
ctagcttcac ctatgctcag cagaaggaga agcccctagt tcaagagaag cagcacccac      60
agcctccacc agctcaaaac caaaaccagg tacgctctcc tggagcccca ggcccttga      120 ccctgaagga ggtagaggag ttggagcagc tgacccagca gctgatgcag gacatggaac     180
accctcagag gcagagcgtg gcagtgaatg agtcctgtgg caaatgcaat cagccactgg     240
cccgtgcaca gcctgcggtt cgtgcac                                        267

<210> SEQ ID NO 32
<211> LENGTH: 267
<212> TYPE: DNA
<213> ORGANISM: Artificial Sequence
<220> FEATURE:
<223> OTHER INFORMATION: Description of Artificial Sequence: Consensus
      sequence
<221> NAME/KEY: modified_base
<222> LOCATION: (1)..(267)
<223> OTHER INFORMATION: "n" represents a, t, c, g, other or unknown

<400> SEQUENCE: 32
ctagcttcac ctatgctcag cagaaggaga agcccctagt tcaagagaag cagcacccac      60
ngcctccacc anctcaaaac caaaaccagn tacgntctcn tgnagnccca gncccnttna     120
ccntnangna gntnnannan ttgnannann tnaccnnnna nntnntnnng nacntggann     180
accntcagag gcagagcgtg gcagtnaatg agtcctgtgg caaatgcant canccactgg     240
cccgngcaca gcctncngtn cgtgcac                                        267
```